(12) United States Patent
MacFarlan et al.

(10) Patent No.: US 6,428,807 B1
(45) Date of Patent: *Aug. 6, 2002

(54) CHELATING IMMUNOSTIMULATING COMPLEXES

(75) Inventors: Roderick Ian MacFarlan, Balwyn; Jim Malliaros, Carnegie, both of (AU)

(73) Assignee: CSL Limited, Parkville (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,309

(22) PCT Filed: Feb. 13, 1998

(86) PCT No.: PCT/AU98/00080

§ 371 (c)(1),
(2), (4) Date: Aug. 11, 1999

(87) PCT Pub. No.: WO98/36772

PCT Pub. Date: Aug. 27, 1998

(30) Foreign Application Priority Data

Feb. 19, 1997 (AU) .............................................. PO 5178

(51) Int. Cl.⁷ .......................... A61K 39/39; A61K 9/127
(52) U.S. Cl. ................. 424/450; 424/130.1; 424/184.1; 514/78; 514/22; 514/23; 514/885
(58) Field of Search .............................. 424/450, 184.1, 424/130.1, 812; 514/78, 885, 22, 23

(56) References Cited

U.S. PATENT DOCUMENTS

| | | | | |
|---|---|---|---|---|
| 5,238,836 A | * | 8/1993 | Certa | 435/252.3 |
| 5,620,690 A | * | 4/1997 | Kersten | 426/184.1 |

FOREIGN PATENT DOCUMENTS

| | | |
|---|---|---|
| EP | 0 180 564 | 5/1986 |
| JP | 06234659 | * 8/1994 |
| WO | 87/02250 | 4/1987 |
| WO | 93/05789 | 4/1993 |
| WO | 96/09805 | * 4/1996 |
| WO | 96/33739 | 10/1996 |

OTHER PUBLICATIONS

Barr et al.; "ISCOM's (Immunostimulating Complexes): The First Decade"; Immunology and Cell Biology; vol. 74; 1996; pp. 13–25.

* cited by examiner

Primary Examiner—Gollamudi S. Kishore
(74) Attorney, Agent, or Firm—Foley & Lardner

(57) ABSTRACT

An immunostimulating complex matrix comprising a saponin preparation, a sterol and a phospholipid, the matrix further comprising a metal-chelating moiety capable of binding a protein or polypeptide having at least one chelating amino acid sequence in the presence of metal ions. An immunogenic immunostimulating complex which comprises this matrix and an immunogenic protein or polypeptide having at least one chelating amino acid sequence, the protein or polypeptide being bound to the matrix in the presence of metal ions.

20 Claims, 19 Drawing Sheets

Figure 3
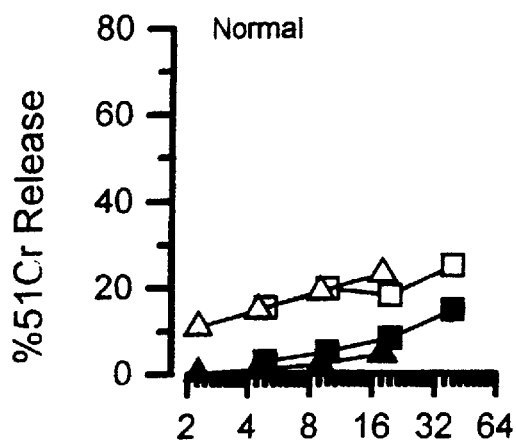
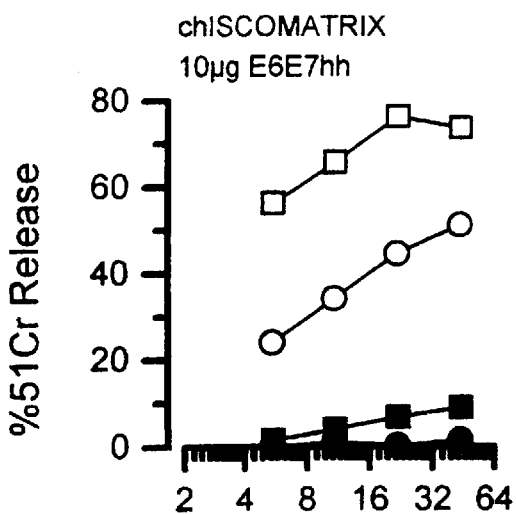
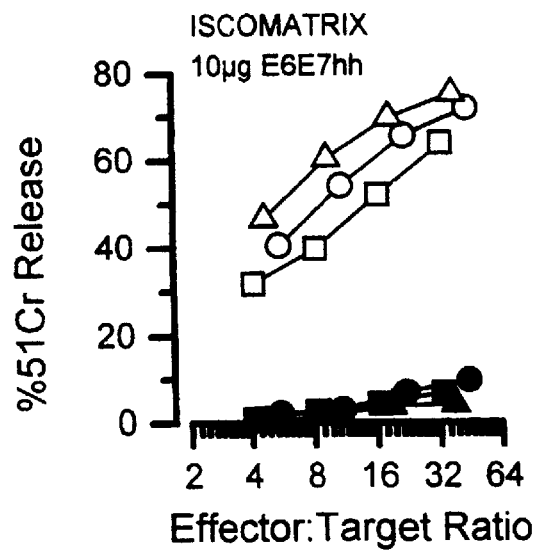
Bottom panel: immunization with ISCOMATRIX mixed with E6E7hh. Centre panel: immunization with chelating ISCOMATRIX plus E6E7hh. Top panel: no immunization.
Symbols represent individual mice, tested against E7-EL4 (open) or OVA-EL4 (closed).

Figure 9
1400µg ISCOPREP703:125µg E6E7hh
Storage at 4°
1400µg ISCOPREP703:125µg E6E7hh
Storage at 31°
1400µg ISCOPREP703:250µg E6E7hh
Storage at 4°
1400µg ISCOPREP703:250µg E6E7hh
Storage at 31°
1400µg ISCOPREP703:500µg E6E7hh
Storage at 4°
1400µg ISCOPREP703:500µg E6E7hh
Storage at 31°
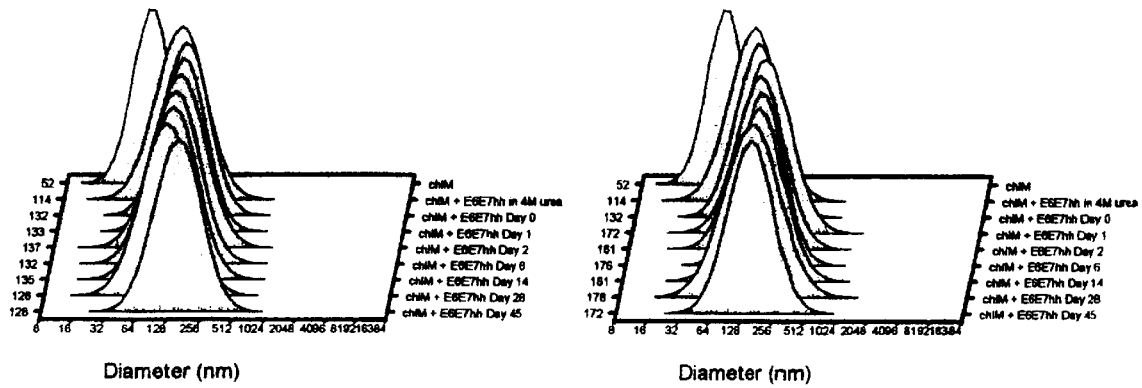
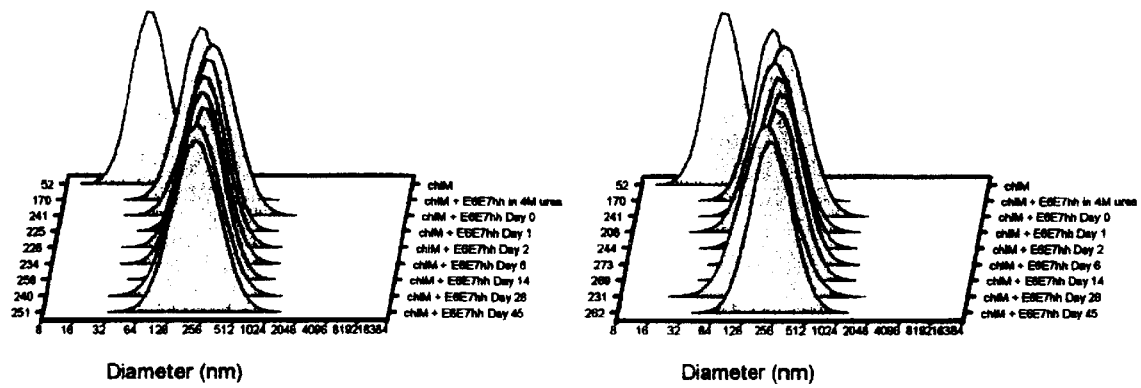
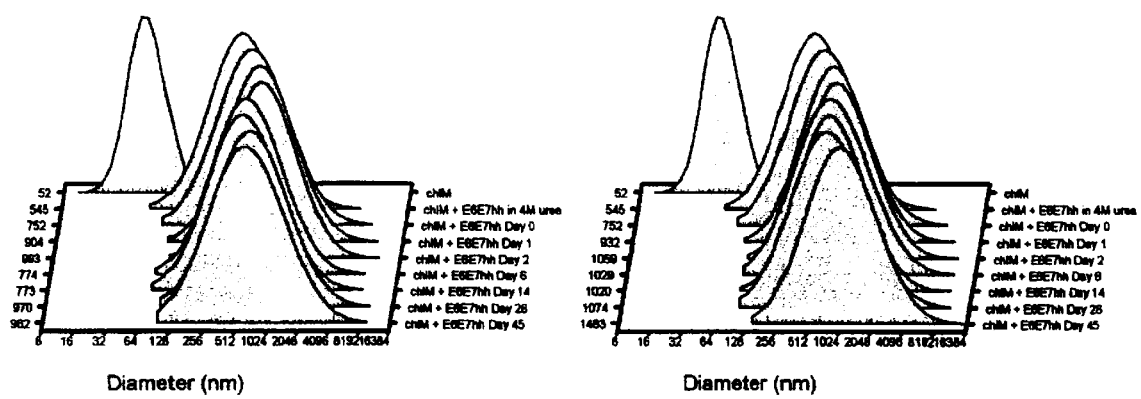

Figure 10A
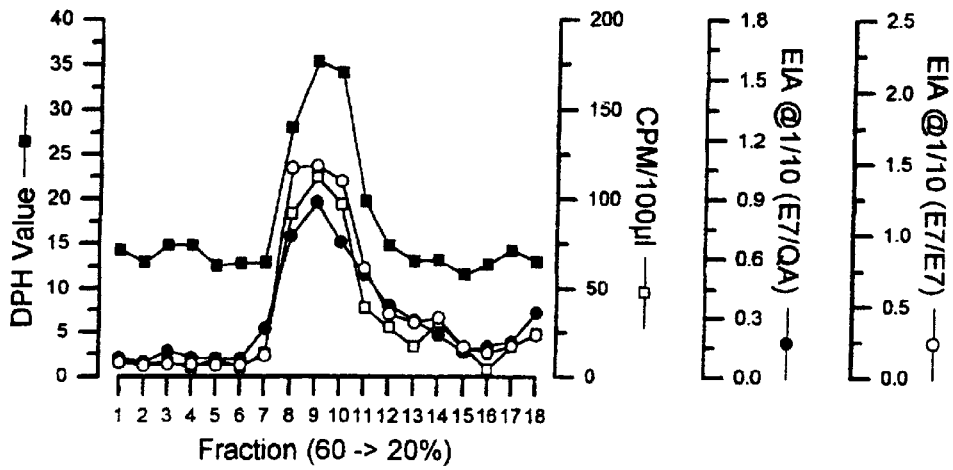
1400:125 Ratio
Day 0
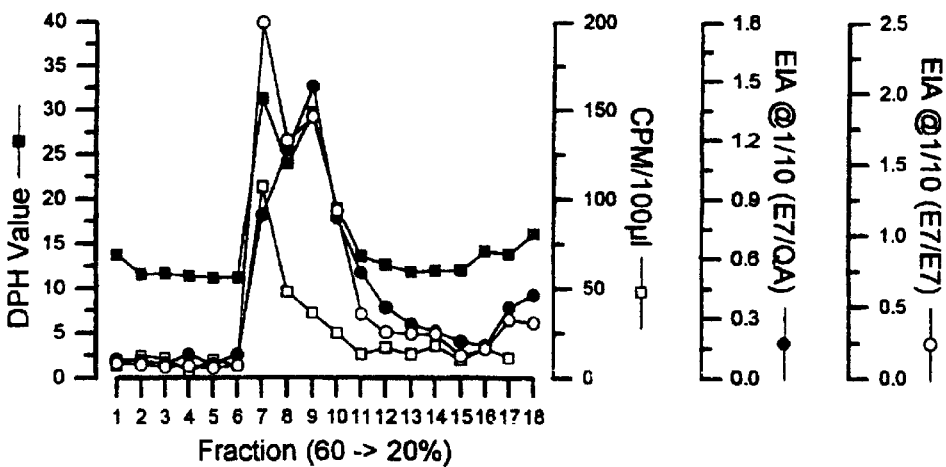
1400:250 Ratio
Day 0
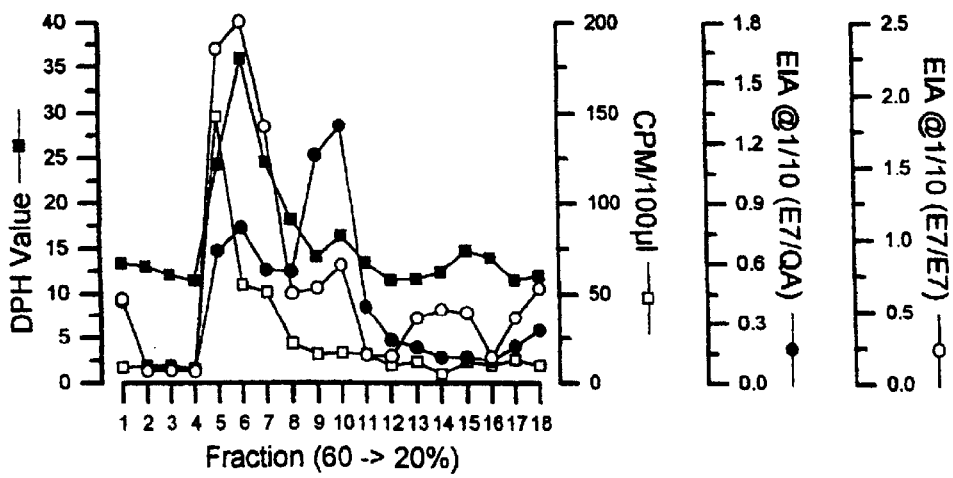
1400:500 Ratio
Day 0

Figure 10B
1400:125 Ratio
Day 6, 4°
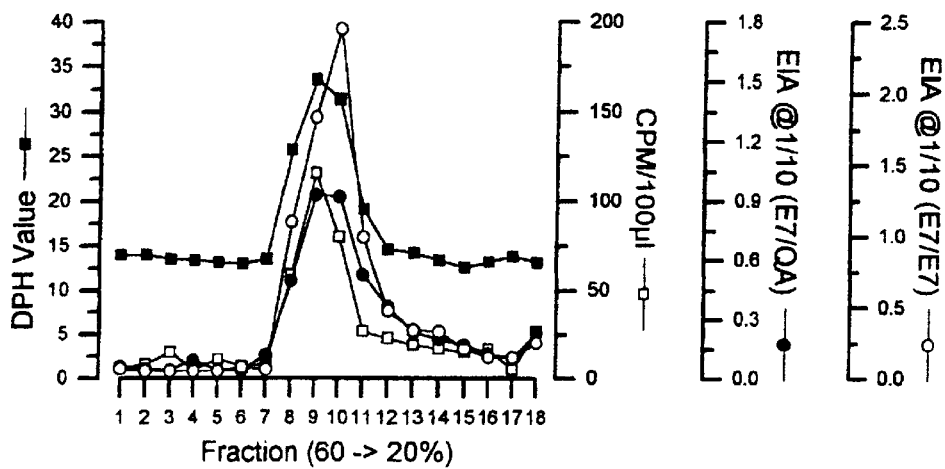
1400:250 Ratio
Day 6, 4°
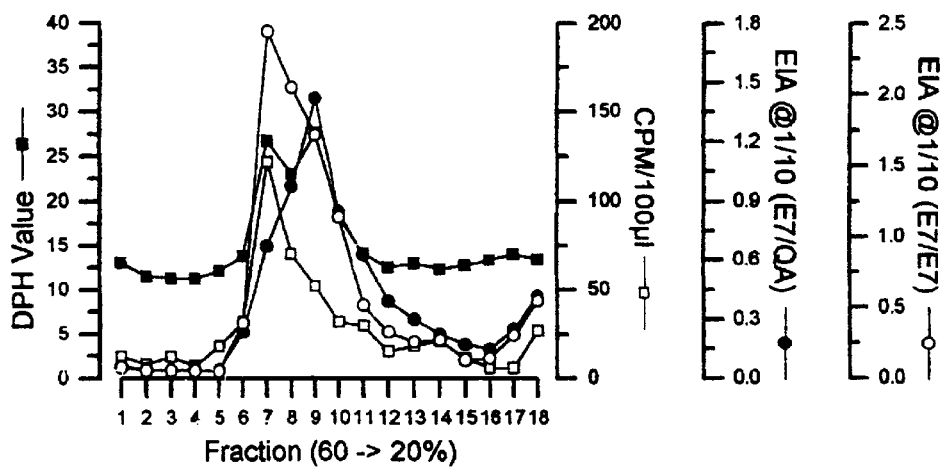
1400:500 Ratio
Day 6, 4°
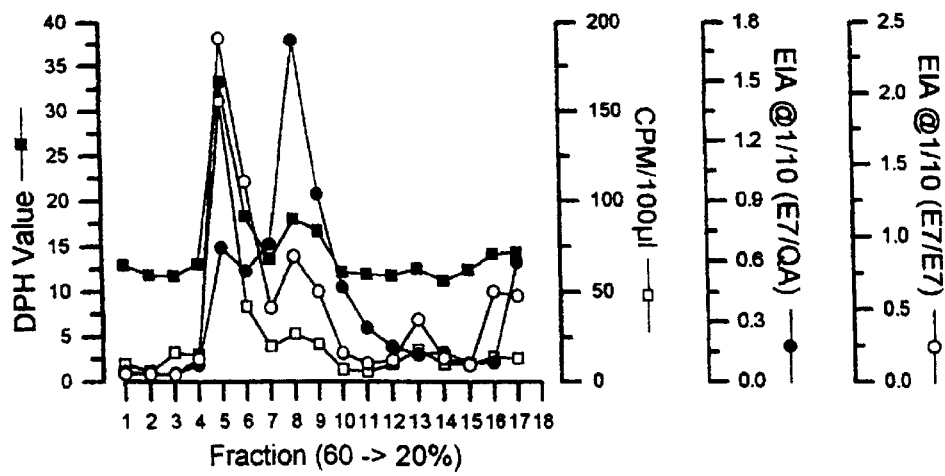

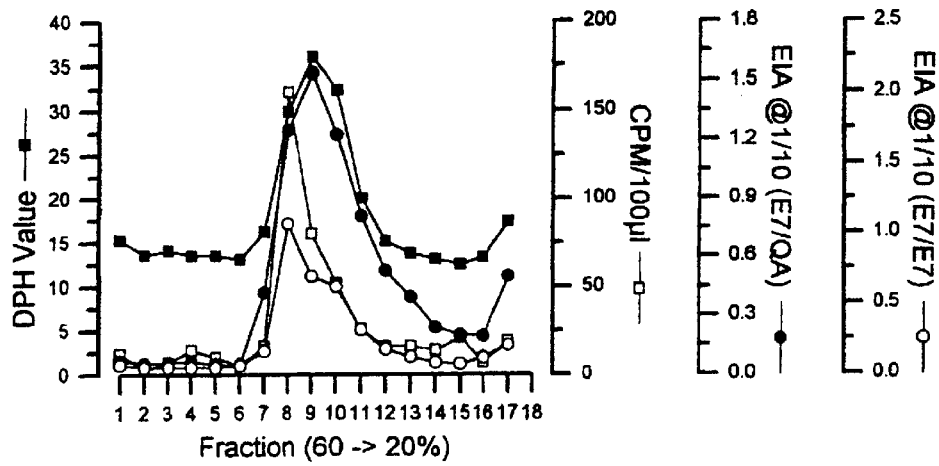
Figure 10C
1400:125 Ratio
Day 6, 31°
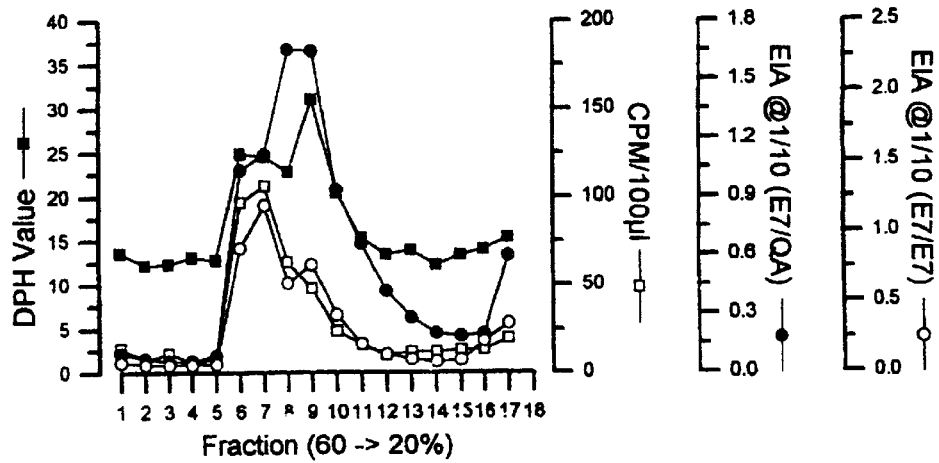
1400:250 Ratio
Day 6, 31°
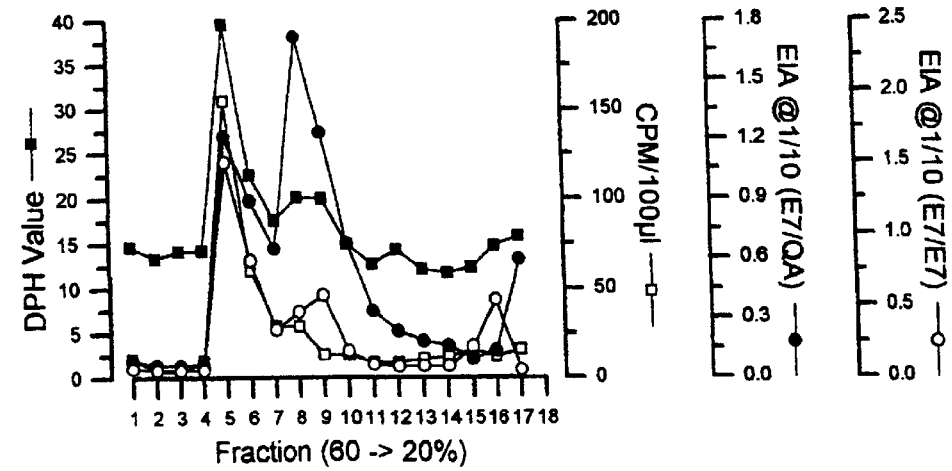
1400:500 Ratio
Day 6, 31°

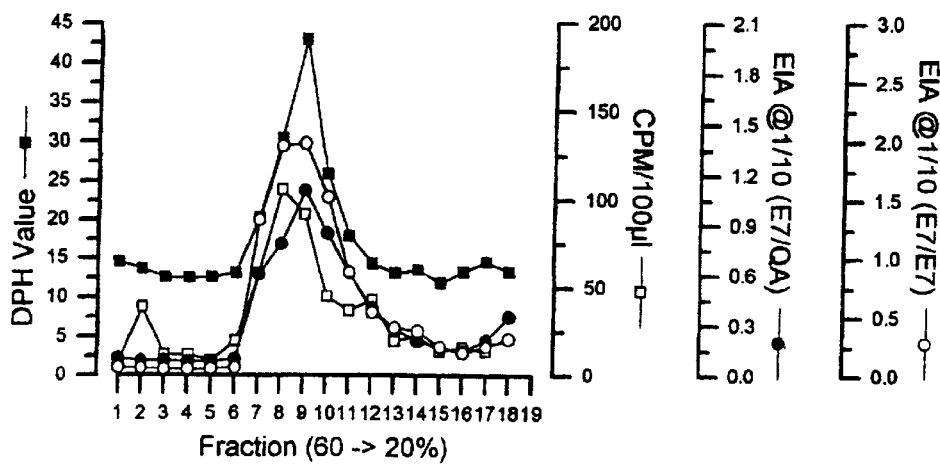
Figure 10D
1400:125 Ratio
Day 45, 4°
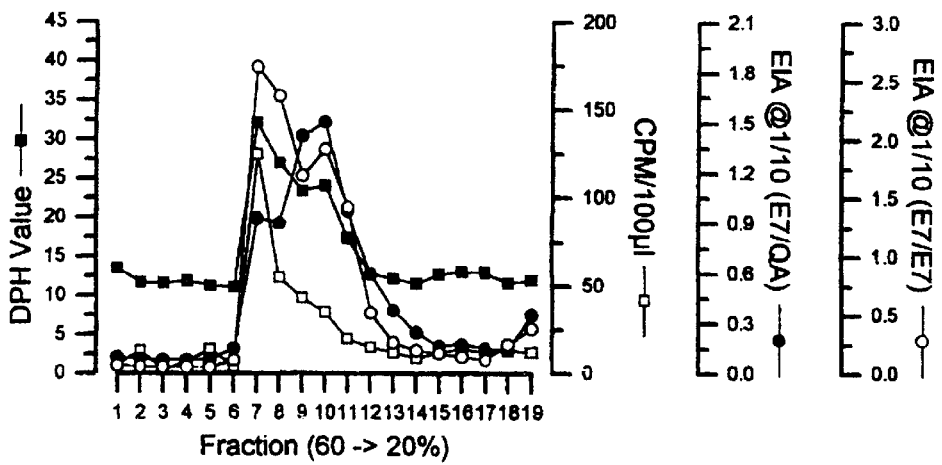
1400:250 Ratio
Day 45, 4°
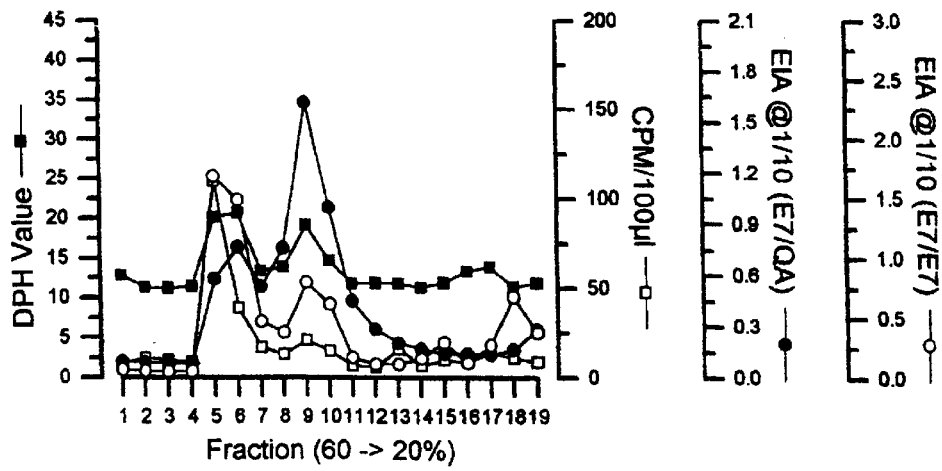
1400:500 Ratio
Day 45, 4°

Figure 10E
1400:125 Ratio
Day 45, 31°
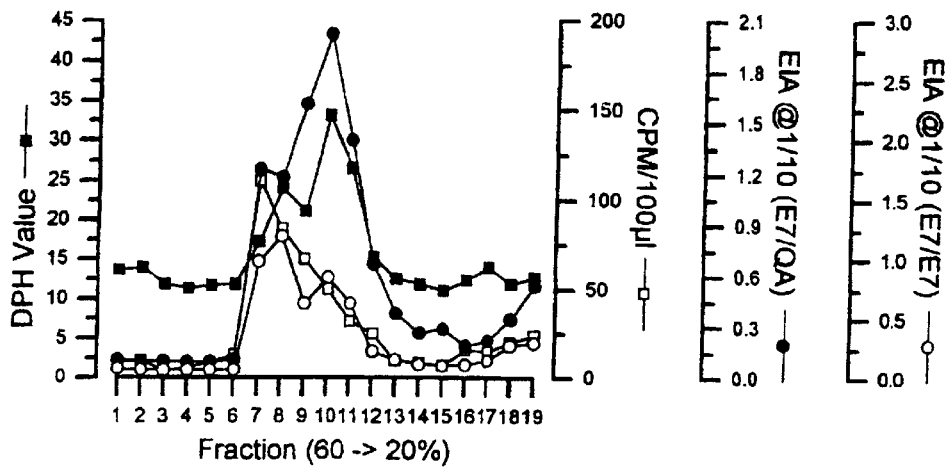
1400:250 Ratio
Day 45, 31°
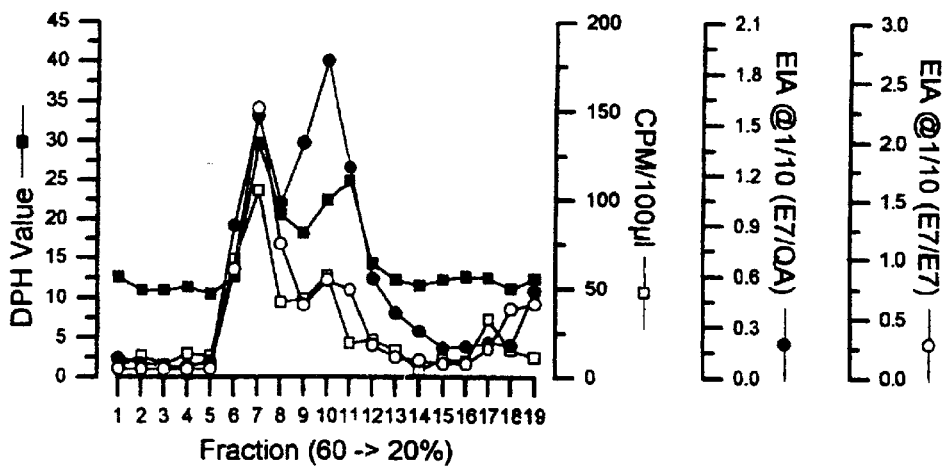
1400:500 Ratio
Day 45, 31°
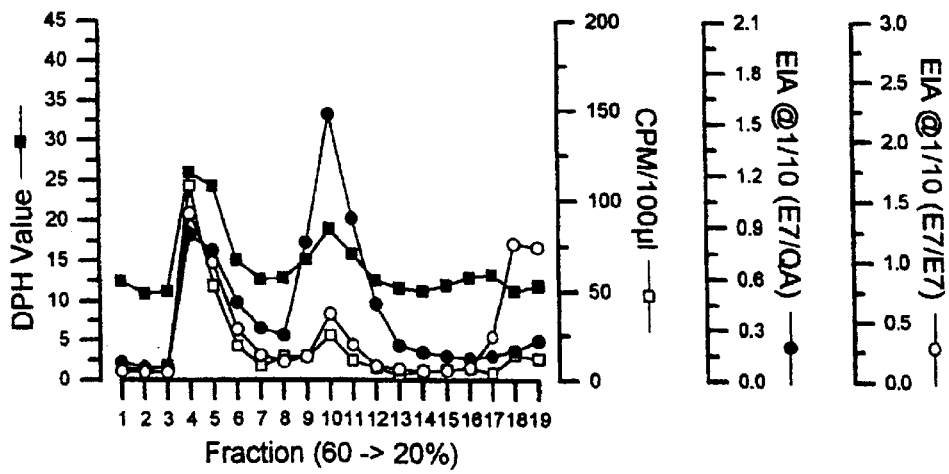

Figure 11
CTL after 2 doses
CTL from individual mice assayed against
EL4/HPV16 E7 (open symbols) or EL4/OVA
(closed symbols) target cells
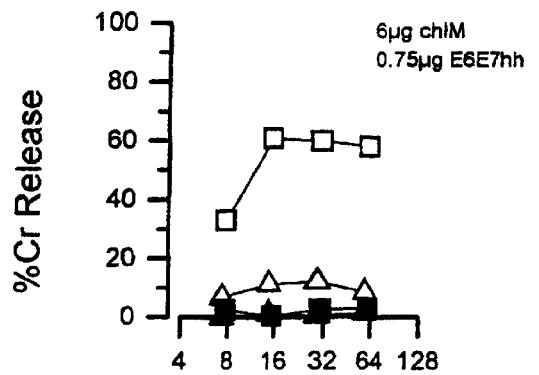
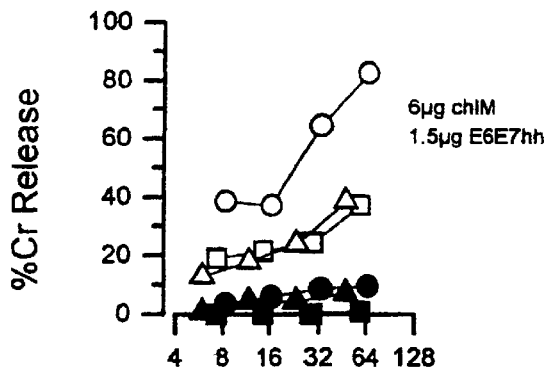
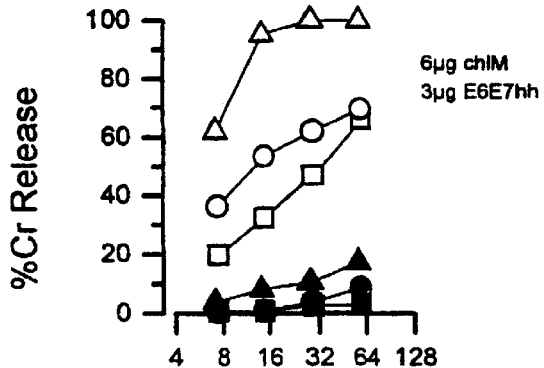
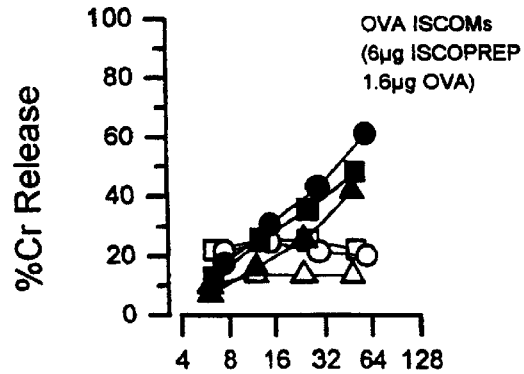
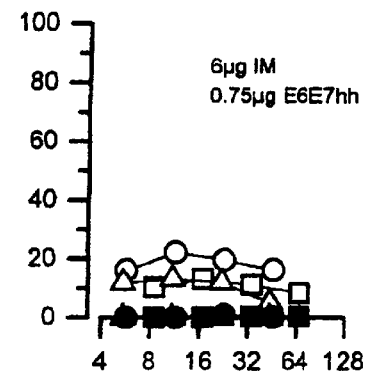
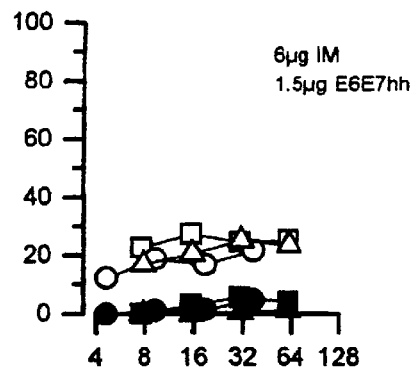
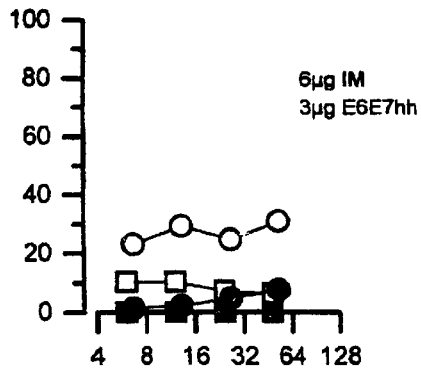
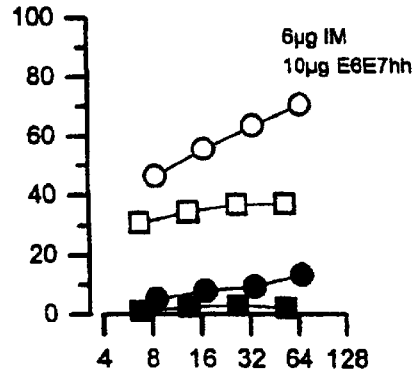

Figure 12 CTL after 3 doses closed bars, 2 immunizations (0.5µg/ml E6E7hh stimulation)
open bars, 3 immunizations (2.5µg/ml GST-E7 stimulation)

CHELATING IMMUNOSTIMULATING COMPLEXES

This application is a 371 of PCT/AU98/00880 filed Feb. 13, 1998.

FIELDS OF THE INVENTION

This invention relates to immunostimulating complex (ISCOM) matrices prepared using saponin preparations, particularly saponin preparations derived from the bark of *Quillaja saponaria* (Molina). The invention also extends to immunogenic immunostimulating complexes in which immunogens are incorporated into an immunostimulating complex matrix in accordance with this invention. Such immunogens may be proteins or polypeptides derived from bacteria, viruses or other microorganisms, but they may, in addition, be synthetic, particularly recombinant proteins, or polypeptides which can induce an immune response.

BACKGROUND OF THE INVENTION

The adjuvant properties of saponin have been long known, as has its abiiity to increase antibody titres to immunogens. As used herein, the term "saponin" refers to a group of surface-active glycosides of plant origin composed of a hydrophilic region (usually several sugar chains) in association with a hydrophobic region of either steroid or triterpenoid structure. Although saponin is available from a number of diverse sources, saponins with useful adjuvant activity have been derived from the South American tree *Quillaja saponaria* (Molina). Saponin from this source was used to isolate a "homogeneous" fraction denoted "Quil A" (Dalsgaard, 1974).

Dose-site reactivity is a major concern for both the veterinary and human use of Quil A in vaccine preparations. One way to avoid this toxicity of Quil A is the use of immunostimulating complexes (known as ISCOMs, an abbreviation for Immuno Stimulating COMplexes). This is primarily because Quil A is less reactive when incorporated into immunostimulating complexes, because its association with cholesterol in the complex reduces its ability to bind to cholesterol in cell membranes and hence its cell lytic effects. In addition, a lesser amount of Quil A is required to generate a similar level of adjuvant effect. Immunostimulating complexes are small, cage-like structures 30 to 40 nm in diameter which retain this structure on freeze drying. The size can vary however depending on mode of preparation, composition and the method used for measurement. The final formulation of a typical immunostimulating complex with an optimal amount of immunogenic protein or polypeptide is a weight ratio of Quil A, cholesterol, phospholipids, and protein or polypeptide (5:1:1:1). Such a typical immunostimulating complex is estimated to contain around 60% by weight Quil A, around 10% each for cholesterol and phospholipids, and the remainder protein or polypeptide. Proteins or polypeptides can be incorporated into the immunostimulating complex matrix either directly or by chemical coupling to a carrier protein (e.g. influenza envelope protein) after incorporation of the carrier protein into the immunostimulating complex.

As an adjuvant, the immunostimulating complex matrix confers many advantages including powerful immunostimulatory effects, low toxicity, ability to induce both cellular (including CTL) and humoral responses, and it is inexpensive in both reagent and manufacturing cost. However, in the past, immunostimulating complexes have had two major disadvantages; firstly, the Quil A used in their preparation was a complex and ill-defined mixture of a biologically-derived product, and batch-to-batch variation was therefore to be expected; and secondly, the complexes still showed reduced but measurable haemolytic activity which could be expected to indicate a certain level of dose-site reactivity.

Since the recognition of the adjuvant activity of Quil A (Dalsgaard, 1974) several groups have further fractionated this material into a number of "purified" components (Australian Patent Specification No. 632067; Kersten, 1990; Kensil, 1988; Kensil 1991). These components were subsequently shown to have variable properties especially in regards to adjuvant activity, haemolytic activity and ability to form immunostimulating complexes. The use of defined or purified saponin components conferred two potential advantages for their use in a human vaccine. Firstly, these components could be characterised and therefore made reproducibly; and secondly, the components could be selected for optimal usefulness.

The immunomodulatory properties of the Quil A saponins and the additional benefits to be derived from these saponins when they are incorporated into an immunostimulating complex have been described in various publications, e.g. Cox and Coulter, 1992; Dalsgaard, 1974; Morein et al., Australian Patent Specifications Nos. 558258, 589915, 590904 and 632067. In Australian Patent Specification No. 632067, the separation of a preparation of Quil A into three distinct fractions called B4b, B3 and B2 is described, along with HPLC chromatographic procedures for this fractionation.

One of the most useful methods for producing recombinant proteins or polypeptides for vaccine (and other) purposes relies on the incorporation of a metal-chelating sequence (usually polyhistidine) at the N- or C-terminus of the recombinant product. This allows facile purification of the product by Immobilized Metal Affinity Chromatography (IMAC), and is especially useful in cases where the protein or polypeptide requires the presence of strong denaturants (such as urea) for solubility (Porath, 1992). Such proteins or polypeptides, however, are difficult to formulate as vaccines using immunostimulating complex (ISCOM) technology. This is because:

1. in many cases removal of the denaturant results in precipitation of the protein or polypeptide—the alternative is not to remove the denaturant, however this may result in unacceptable toxicity of the vaccine or poor stability of vaccine formulations; and
2. it is difficult to efficiently incorporate such proteins or polypeptides in immunostimulating complex matrices, since this requires that the protein or polypeptide be ampipathic in character—this is a property of proteins that span cell membranes, but very few other proteins.

Incorporation of proteins or polypeptides into immunostimulating complex has two major benefits:

1. the extremely hydrophilic character of the matrix particle will prevent the precipitation of hydrophobic proteins or polypeptides that are insoluble in the absence of denaturant; and
2. incorporation of the protein or polypeptide into immunostimulating complexes will provide the maximum adjuvant effect. This is especially the case for cytotoxic T-lymphocyte responses, where codelivery of saponin and immunogen to the same antigen-presenting cell may be an absolute requirement for obtaining an adequate immune response. Clearly, codelivery will be much more efficient if the protein or polypeptide is anchored in an immunostimulating complex.

It is an object of the present invention to provide a simple and effective method for incorporating a protein or polypeptide, particularly a metal-chelating protein or polypeptide, into immunostimulating complex matrix particles.

Shnek et al. (1994) disclose a method for targeting proteins to lipid assemblies known as liposomes using a phospholipid-like molecule in which the head group is a chelating iminodiacetic acid (IDA), and show that such liposomes can bind histidine-rich myoglobin in the presence of metal ions.

SUMMARY OF THE INVENTION

According to the present invention, there is provided an immunostimulating complex matrix comprising a saponin preparation, a sterol and a phospholipid, said matrix further comprising a metal-chelating moiety capable of binding a protein or polypeptide having at least one chelating amino acid sequence in the presence of metal ions.

In another aspect, the present invention also provides an immunogenic immunostimulating complex which comprises a matrix as broadly described above and an immunogenic protein or polypeptide having at least one chelating amino acid sequence, said protein or polypeptide being bound to said matrix in the presence of metal ions.

BRIEF DESCRIPTION OF THE DRAWINGS

FIG. 3 shows CTL responses the testing of cells for CTL using E7—and OVA-expressing EL4 cells as targets. A: no immunization; B: ChIMX-E6E7hh; C: IMX-E6E7hh. ○, □, ◊-killing of E7-transfected cells; individual mice. ●, ■, ▲—killing of OVA transfected cells; individual mice.

FIG. 9 shows the effect upon matrix particle size of the protein: matrix ratio, presence of urea and storage at 4° C. or 31° C. for up to 45 days after urea removal by dialysis.

FIGS. 10A–E show the analysis of sucrose gradient fractions of the preparations from FIG. 9. A: day O; B: storage at 4° C. for 6 days, C: storage at 31° C. for 6 days, D: storage at 4° C. for 45 days, E: storage at 31° C. for 45 days.

FIG. 11 shows CTL responses after two doses of A, C, E: ChIMX and E6E7hh at 0.75, 1.5 and 3.0 μg respectively, G: target cell positive control, B, D, F, H: IMX and E6E7hh at 0.75, 1.5, 3.0 and 1 0.0 μg respectively. ○, □, ◊—killing of E7 transfected cells; individual mice; ●, ■, ▲—killing of OVA transfected cells; individual mice.

DETAILED DESCRIPTION OF THE INVENTION

Figure 1:
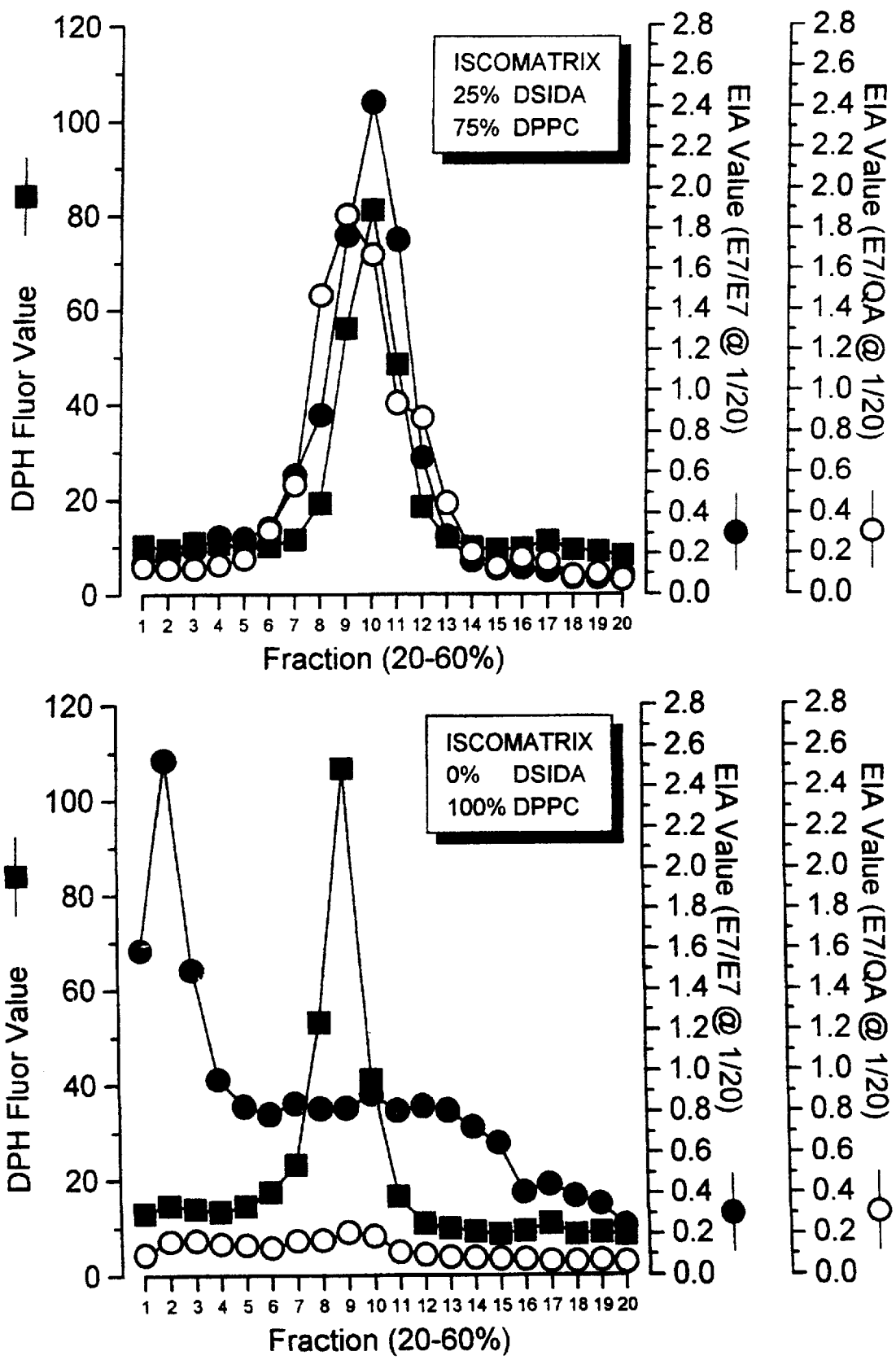
FIG. 1 shows the analysis of sucrose gradient fractions of A: Chelating Iscomatrix (ChIMX) mixed with E6E7hh; B: lscomatrix (IMX) mixed with E6E7hh. ○ E6E7hh associated with matrix; ● total E6E7hh; ■ matrix.

As described above, the present invention provides a method of incorporating a protein or polypeptide having at least one chelating amino acid sequence into an immunostimulating complex matrix. In a preferred aspect, the present invention is directed to incorporating into an immunostimulating complex matrix a recombinant protein or polypeptide incorporating a polyhistidine or other metal-chelating sequence, allowing purification of the recombinant product by IMAC.

In accordance with the invention, the immunostimulating complex matrix is prepared in such a way that there is an exposed metal-chelating moiety able to spontaneously bind the recombinant product in the presence of appropriate metal ions. In order to provide this metal-chelating moiety, an appropriate molecule is incorporated into the matrix which preferably comprises three functional domains:

(a) a hydrophobic sequence which anchors the molecule in the matrix;

(b) a metal-chelating headgroup; and optionally, (c) a spacer region which separates the chelating headgroup from the surface of the matrix.

Particularly suitable compounds include phospholipid-like molecules in which the metal-chelating headgroup is a chelating iminodiacetic acid (IDA), such as 1,2-distearyl-rac-glycerol-3-(8-(3,6-dioxy)octyl-1-amino-N,N-diacetic acid (abbreviated as DSIDA), having the structure shown in Formula I (Shnek et al., 1994; Ng et al., 1995):

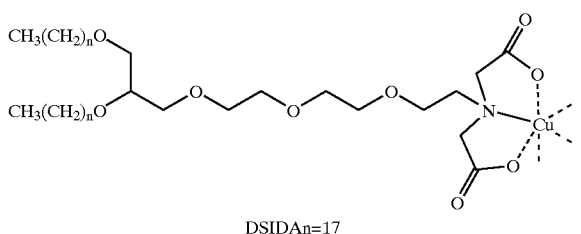

DSIDA n=17

Formula I

This is essentially a phospholipid like molecule, in which the head group is a chelating iminodiacetic acid (IDA), separated from a diacyl C18 tail by a triethylene glycol spacer (10 atoms).

Alternatively, a similar molecule to DSIDA in which the diacyl C18 tail is replaced by a diacyl C16 tail (Formula I, n=15), known as DPIDA (Pack and Arnold, submitted) may be used.

Another group of components which are suitable for incorporation into immunostimulating complex matrices in accordance with this invention are phospholipid-like molecules in which the metal-chelating head group is N-nitrilotriacetic acid (see, for example, Schmitt et al., 1994; Kubalek et al., 1994; Dietrich et al., 1995; Dietrich et al., 1996). Additionally, any of the metal-chelating headgroups that have been used for IMAC may be used (Porath, 1992).

There have been many prior attempts to incorporate immunogenic proteins or polypeptides into immunostimulating complexes. Techniques tried include direct covalent chemical coupling onto the immunostimulating complex matrix or onto influenza immunostimulating complexes, low pH or chaotropic ion treatment of the protein or polypeptide to expose hydrophobic regions normally internalized and chemical attachment of fatty acids to the protein or polypeptide. All of these methods suffer from the disadvantage that they are either uncontrollable or difficult to control, and are difficult or impossible to apply to proteins or polypeptides soluble only in denaturant.

The present invention provides a simple and generic process whereby any recombinant (or indeed natural) protein possessing chelating amino acid sequences can be incorporated into immunostimulating complexes, with the consequent benefits of improved immunogenicity and solubility.

In the case of recombinant proteins engineered to contain a single polyhistidine sequence, the invention enables ordered and unequivocal assembly of the protein immunostimulating complex. This contrasts with methods such as chemical modification of the lysine-side chains of protein with fatty acid, which are random and uncontrollable.

The precise nature of the protein or polypeptide is immaterial to the present invention, and the invention extends to immunogenic proteins or polypeptides from bacterial, viral or other sources. In addition, the present invention is particularly suitable for cancer vaccines which induce a CTL response, for example using insoluble recombinant proteins such as the MAGE family of tumor antigens.

The saponin preparation in the immunostimulating complex matrix of this invention may be Quil A (Dalsgaard, 1974) or purified components thereof as previously described in Australian Patent Specification No. 632067 in the name of Morein et al., Kersten, 1990, Kensil, 1988 or Kensil, 1990. Alternatively, the preparation may be a composition comprising from 50 to 90% by weight of Fraction A of Quil A and from 50 to 10% by weight of Fraction C of Quil A, as described in International Patent Application No. PCT/AU95/00670 (WO 96/1171). A particularly preferred saponin preparation comprises QH703 (70% Fraction A; 0% Fraction B; 30% Fraction C), known as ISCOPREP703. The fractionation of crude aqueous Quil A extract to Fractions A, B and C is described in detail in Example 1 of International Patent Application No. PCT/AU95/00670. In general terms, in this fractionation procedure Fractions A, B and C are prepared from the lipophilic fraction obtained on chromatographic separation of the crude aqueous Quil A extract and elution with 70% acetonitrile in water to recover the lipophilic fraction. This lipophilic fraction is then separated by semipreparative HPLC with elution using a gradient of from 25% to 60% acetonitrile in acidic water. The fraction referred to as "Fraction A" or "QH-A" is the fraction which is eluted at approximately 39% acetonitrile. The fraction referred to as "Fraction B" or "QH-B" is the fraction which is eluted at approximately 47% acetonitrile. The fraction referred to as "Fraction C" or "QH-C" is the fraction which is eluted at approximately 49% acetonitrile.

The sterol used in the formation of an immunostimulating complex matrix according to this invention may be cholesterol or any other sterol as known in the art.

Similarly, the phospholipid used in the formulation of the matrix may be a phosphatidyl choline such as dipalmitoyl phosphatidyl choline (DPPC) or any other phospholipid as known in the art. Alternatively, a phospholipid with an ethanolamine head group, such as dipalmitoyl phosphatidyl ethanolamine (DPPE) or distearoyl phosphatidyl ethanolamine (DSPE), may be used.

The matrix or immunogenic immunostimulating complex based thereon may also comprise one or more known adjuvants, immunosuppressive agents or other immunomodulating agents which are effective in enhancing, suppressing or otherwise changing the immune system of a human or animal.

An immunostimulating complex matrix or an immunogenic immunostimulating complex in accordance with the present invention may be prepared by techniques which are well known to persons skilled in the art, and which are described in detail in the publications Cox and Coulter, 1992 and Australian Patent Specifications Nos. 558258, 589915, 590904 and 632067, the disclosures of which are incorporated herein by reference.

The immunogen which is incorporated into the immunostimulating complex matrix in accordance with this invention may be any chemical entity which can induce an immune response, including but not limited to proteins and polypeptides derived from bacteria, viruses or other microorganisms.

The immunogen, which is preferably a recombinant protein or polypeptide incorporating a polyhistidine sequence or other sequence able to chelate metal ions, is bound to the matrix in the presence of metal ions, particularly divalent metal ions such as $Cu^{++}$, $Ni^{++}$, $Zn^{++}$ and $Co^{++}$. The metal chelating moiety in the matrix is selected to bind the metal ions tightly, yet leave sites available for binding to the polyhistidine (for example penta-his or hexa-his) or other chelating amino acid sequence on the protein or polypeptide.

The present invention also extends to a vaccine composition for use in eliciting an immune response in humans or animals comprising as the active component thereof an immunogenic immunostimulating complex as broadly described above, together with one or more pharmaceutically and/or veterinarily acceptable carriers and/or diluents.

Suitable pharmaceutically and/or veterinarily acceptable carriers and/or diluents for use in such vaccine compositions are well known in this art and are described by way of example in *Remington's Pharmaceutical Sciences,* 18th Edition, Mack Publishing Company, Pennsylvania, USA.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In yet another aspect, this invention extends to a method of eliciting an immune response in humans or animals, which comprises the administration of an immunologically effective amount of an immunogenic immunostimulating complex as broadly described above.

By the use of the term "immunologically effective amounts" herein, it is meant that the administration of that amount to a human or animal, either in a single dose or as part of a series, which is effective in eliciting an immune response in the human or animal to the immunogen(s) in the vaccine composition. This amount varies depending upon the health and physical condition of the individual to be treated, the taxonomic group of individual to be treated, the capacity of the individual's immune system to respond to the vaccine composition, the degree of protection desired, the formulation of the vaccine, the assessment of the medical situation and other relevant factors. It is expected that the amount will fall in a relatively broad range that can be determined through routine trials.

The invention also extends to the use of an immunogenic immunostimulating complex as broadly described above in the manufacture of a composition for use in eliciting an immune response in humans or animals.

Throughout this specification, unless the context requires otherwise, the word "comprise", or variations such as "comprises" or "comprising", will be understood to imply the inclusion of a stated integer or group of integers but not the exclusion of any other integer or group of integers.

ISCOM, ISCOPREP, ISCOPREP703 and ISCOMATRIX used herein are trade marks of CSL Limited, Melbourne, Australia.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

ISCOMATRIX consists of a purified and well characterized mixture of Quillaja saponins known as ISCOPREP703, cholesterol, and dipalmitoyl phosphatidyl choline (DPPC). These components are combined in a detergent-containing buffer, and dialysed to form ISCOMATRIX particles typically of 40–80 nm diameter.

Chelating ISCOMATRIX was formed in a similar fashion, except that DSIDA and copper were added to the formulation. In detail:

The following solutions were prepared:
1. 5 mg/ml cholesterol, 3.33 mg/ml DPPC, 160 mg/ml Mega-10 in water
2. 50 mg/ml ISCOPREP703 in water
3. 20 mM bisTRIS, 150 mM NaCl, pH6.8 (passed through a Chelex column to remove contaminating metal ions)
4. 3.33 mg/ml DPPC, 1 mg/ml $Cu(Cl)_2.2H_2O$, in 90% chloroform/10% methanol
5. 3.83 mg/ml DSIDA, 1 mg/ml $Cu(Cl)_2.2H_2O$, in 90% chloroform/10% methanol These solutions were combined while mixing in the following order:

Preparation A
1.7 ml of #3
0.2 ml of #1
0.1 ml of #4 (DPPC)
chloroform removed by evaporation with a stream of nitrogen
0.1 ml of #2

Preparation B
1.7 ml of #3
0.2 ml of #1
0.025 ml of #4 (DPPC)
0.075 ml of #5 (DSIDA)
chloroform removed by evaporation with a stream of nitrogen
0.1 ml of #2

The final composition of the mixtures were:

|  | Preparation A (no DSIDA) | Preparation B (25% mole ratio of DSIDA to DPPC) |
| --- | --- | --- |
| ISCOPREP703 | 2.5 mg/ml | 2.5 mg/ml |
| cholesterol | 0.5 mg/ml | 0.5 mg/ml |
| DPPC | 0.5 mg/ml | 0.375 mg/ml |
| DSIDA | not added | 0.144 mg/ml |
| $Cu(Cl)_2.2H_2O$ | 0.05 mg/ml | 0.05 mg/ml |
| Mega-10 | 16 mg/ml | 16 mg/ml |

The mixtures were incubated for 1 hr at room temperature, then dialysed against 4 liters of phosphate buffered saline pH 6.9 at room temperature for 24 hr using 10,000 molecular weight cutoff dialysis membrane. This was repeated for an additional 24 hr at 4°.

The preparations were then characterized by photon correlation spectroscopy using a Nicomp370 analyzer, and the mean particle diameter calculated following Gaussian analysis of the intensity weighted data. Preparation A (no DSIDA) was 61.3 nm, and preparation B (25% mole ratio of DSIDA to DPPC) was 67.2 nm. These values are within the range expected for ISCOMATRIX.

EXAMPLE 2

In order to determine whether the ISCOMATRIX preparations of Example 1 could bind protein, 0.3 ml of either preparation A or preparation B was mixed with 15 μg of polyhistidine-containing protein in 0.3 ml of 8M urea, 0.3 M NaCl, 50 mM bisTRIS pH 7.0.

The polyhistidine-containing protein used in this example consisted of the E6 and E7 open reading frames of human papillomavirus 16, as a fusion protein with a carboxy terminal hexa-histidine sequence. The primary amino acid sequence is:
M H Q K R T A M F Q D P Q E R P R K L P Q L C T E L Q T-
T I H D I I L E C V Y C K Q Q L L R R E V Y D-

FAFRDLCIVYRDGNPYAVCDKCLK-
FYSKISEYRHYCYSLYGTTLEQQYNKPLCDLLIR
CINCQKPLCPEEKQRHLDKKQRFHNIR-
GRWTGRCMSCCRSSRTRRETQLPGMH-
GDTPTLHEYMLDLQPETTDLY-
CYEQLNDSSEEEDEIDGPAGQAEPDRAHYNIVT
FCCKCDSTLRLCVQSTHVDIRTLEDLL-
MGTLGIVCPICSQKPRSHHHHHH (SEQ ID NO. 1)

The preparation used was purified from *E. coli* inclusion bodies, following sulfonation of cysteine residues, by a combination of IMAC and size exclusion chromatography. Analysis on SDS PAGE indicated that the material used was of greater than 95% purity.

After 4 hr incubation at room temperature, the mixtures were applied to the top of a 20–60% w/w gradient of sucrose in phosphate buffered saline, and centrifuged at 35,000 rpm for 17 hr in a Beckman SW40 rotor. Individual fractions were collected and assayed for the presence of ISCOMATRIX, for the presence of total recombinant polyhistidine-containing HPV16 E6E7hh, and for the presence of recombinant polyhistidine-containing HPV16 E6E7hh that was associated with ISCOMATRIX.

The assays used were:

1. For ISCOMATRIX: the increase in quantum yield of the fluorescent probe diphenylhexatriene (DPH) on transfer from the aqueous phase to the lipophilic ISCOMATRIX environment was measured.

In Detail

1. Weigh approx. 1–2 mg of DPH into a glass vial, and dissolve in acetone at 1 mg/ml.
2. Dilute the DPH/acetone solution 1 in 50 in PBS 0.1% azide pH 7.2. The solution should go cloudy.
3. Mix 50 $\mu$l of each fraction and 50 $\mu$l of the DPH in PBS in wells of a microtiter plate, and incubate at room temp. for 150 min.
4. Read in the Fluoroskan using ex 355 nm/em 460 nm (results can be read at other time points, however the signal does increase with time).
5. Express results as fluor units. This is sufficient to locate the peak in a centrifugation/gel filtration experiment.

2. For total recombinant polyhistidine-containing HPV16 E6E7hh:

A two site EIA was used. Aliquots of each fraction were added to wells of a microtiter plate coated with monoclonal antibody LHIL-16E76D (specific for HPV16 E7) Following a series of washes and incubations, bound HPV 16 E7 was detected with a second monoclonal antibody (LHIL-16E78F, specific for HPV16 E7) which had been chemically conjugated with the enzyme horse radish peroxidase (HRP). The amount of bound HPV 16 E7 is proportional to the enzymic activity of HRP remaining in the microtiter plate following additional washes and incubations. This is conveniently measured by a color change following incubation with a substrate of HRP.

3. For recombinant polyhistidine-containing HPV16 E6E7hh associated with ISCOMATRIX:

A two site EIA was used. Aliquots of each fraction were added to wells of a microtiter plate coated with monoclonal antibody LHIL-16E76D (specific for HPV16 E7). Following a series of washes and incubations, bound HPV16 E6E7hh associated with ISCOMATRIX was detected with a second monoclonal antibody (DD15.5G11, specific for an epitope of Quillaja saponin detectable on the surface of ISCOMATRIX), which had been chemically conjugated with the enzyme horse radish peroxidase (HRP). The amount of enzymic activity of HRP remaining in the microtiter plate following additional washes and incubations is indicative of the amount of HPV16 E6E7hh associated with ISCOMATRIX. This is conveniently measured by a color change following incubation with a substrate of HRP.

FIG. 1 shows the analysis of sucrose gradient fractions by these three assays. For both preparations A (0% DSIDA) and B (25% DSIDA), there is a single well defined ISCOMATRIX peak centered on fractions 9–10. In preparation A(0% DSIDA) total E6E7hh is distributed through the gradient, with a peak at the top of the gradient representing material in urea that has not entered the gradient. There is no peak corresponding to ISCOMATRIX-associated E6E7hh. In contrast, all of the detectable E6E7hh in preparation B (25% DSIDA) is associated with the ISCOMATRIX peak and this is almost exactly coincident with the ISCOMATRIX-associated E6E7hh. This is clear evidence that ISCOMATRIX formulated with DSIDA and charged with $Cu^{++}$ binds polyhistidine-containing protein. Furthermore, under these experimental conditions, all of the added protein has been bound.

EXAMPLE 3

The chelating ISCOMATRIX prepared in Example 1 using DSIDA has been tested for capacity to induce a cytotoxic T-lymphocyte (CTL) response in order to demonstrate its potential as a vaccine adjuvant.

The E6E7hh plus chelating ISCOMATRIX formulation which was analysed by density gradient centrifugation in Example 2 was dialysed against 0.5M arginine, 0.5M NaCl, 50 mM sodium phosphate, 10 mM TRIS. The dialysed formulation was diluted to a dosage level estimated to consist of 6 $\mu$g of chelating ISCOMATRIX (as ISCOPREP703), and 2 $\mu$g E6E7hh in 50 $\mu$l (this was calculated based on 66% of the theoretical recovery of the components added to the formulation). The control formulation consisted of 6 $\mu$g of ISCOMATRIX (as ISCOPREP703) mixed with 10 $\mu$g of E6E7hh in 50 $\mu$l of 8M urea, 50 mM TRIS, 0.3M NaCl, pH 7.0, and had been shown previously to induce CTL in this assay system.

Figure 2:
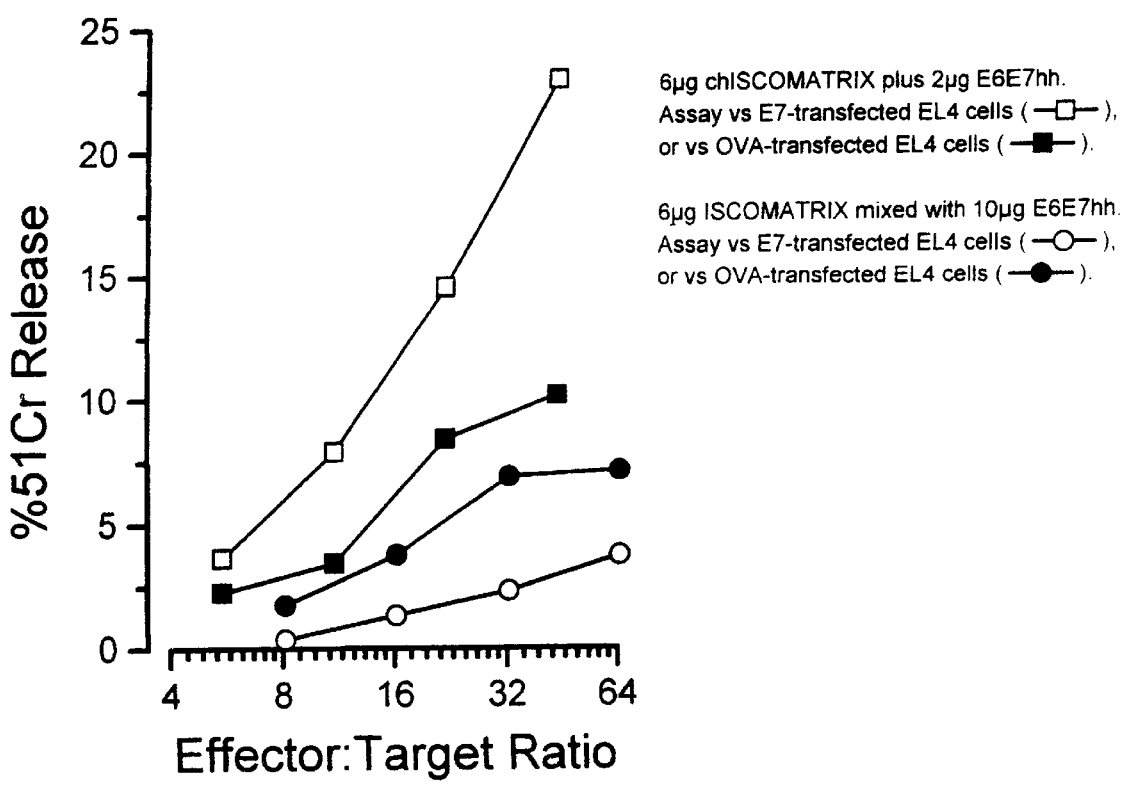
FIG. 2 shows cytotoxic T lymphocyte (CTL) responses and the results of testing the ability of cells cultured from C57BL/6 mice to kill HPV16 E7-expressing EL4 mouse tumor cells. □ ChIMX-E6E7hh killing of E7-transfected cells; ■ ChIMX-E6E7hh killing of OVA transfected cells; ○ IMX-E6E7hh killing of E7-transfected cells; ● IMX-E6E7hh killing of OVA transfected cells.

Four days following inoculation of C57BL/6 mice in the footpad with 50 $\mu$l of each formulation, popliteal lymph node cells were pooled from groups of 4 mice and cultured for an additional 4 days at $3\times10^6$ cells/ml in RPMI1640 with 10% foetal calf serum (FCS) and 20 IU/ml of IL-2 (BioSource CY04010). The cells were then recovered from the cultures and tested for their ability to kill HPV16 E7-expressing EL4 mouse tumor cells (prepared by transfection with DNA coding for HPV16 E7) or control ovalbumin (OVA)-expressing EL4 cells (EG7; an EL4 line transfected with DNA coding for OVA, and obtained from Dr. F. Carbone, Monash University, Melbourne) in a 4 hour $^{51}$Cr-release assay. The results are shown in FIG. 2. In this experiment the levels of cytotoxicity were lower than normally obtained, and in fact no CTL activity was detected in the mice vaccinated with ISCOMATRIX mixed with E6E7hh. However it is clear that the chelating ISCOMATRIX formulation did induce a CTL response which, in this experiment, was better than that induced by ISCOMATRIX mixed with E6E7hh. This was despite the fact that the chelating ISCOMATRIX formulation contained less E6E7hh, and was unoptimised.

In a second experiment, individual C57BL/6 mice were inoculated subcutaneously with either 6 $\mu$g of chelating ISCOMATRIX (prepared with DSIDA) plus 10 $\mu$g of E6E7hh, or 6 $\mu$g of ISCOMATRIX mixed with 10 $\mu$g of E6E7hh. After 3 weeks the mice were boosted with the same dose formulation. The dose compositions were as follows:

|  | chelating ISCOMATRIX plus E6E7hh | ISCOMATRIX mixed with E6E7hh |
| --- | --- | --- |
| E6E7hh | 10 μg/100 μl | 10 μg/100 μl |
| chelating ISCOMATRIX (batch 970224) | 6 μg/100 μl** | nil |
| control ISCOMATRIX (batch 970227) | nil | 6 μg/100 μl** |
| urea | 0.35M | 6.74M |
| arginine | 0.46M | nil |
| TRIS | 0.44 mM | 0.44 mM |
| bisTRIS | 45.6 mM | 45.6 mM |
| sodium phosphate | 2.64 mM | 2.64 mM |
| NaCl | 0.3M | 0.3M |
| pH | 7.0 | 7.0 |

**measured as ISCOPREP703

Seven days after the last dose, mice were evaluated for their responses to E6E7hh. One mouse was excluded from the results on the basis that the spleen cells recovered had poor viability, and were negative in all assays performed, including release of cytokines in response to stimulation with the T-cell mitogen concanavalin A.

CTL were tested following in vitro stimulation of spleen cells from individual mice with mitomycin C-treated E7-expressing EL4 cells. Cultures were for 5 days at 37° in 5% $CO_2$, humidified, in a total volume of 8 ml of RPMI 1640+10% FCS, and included $2.5 \times 10^6$ responder spleen cells/ml, and 0.125×10/ml mitomycin C-treated E7-expressing EL4 cells as stimulators. At the end of the culture period, cells were recovered from the cultures and tested for CTL in a 4 hr $^5$Cr-release assay using E7- and OVA-expressing EL4 cells as targets.

The results are shown in FIG. 3, and clearly demonstrate that chelating ISCOMATRIX plus E6E7hh is effective in inducing a CTL response.

Figure 4:
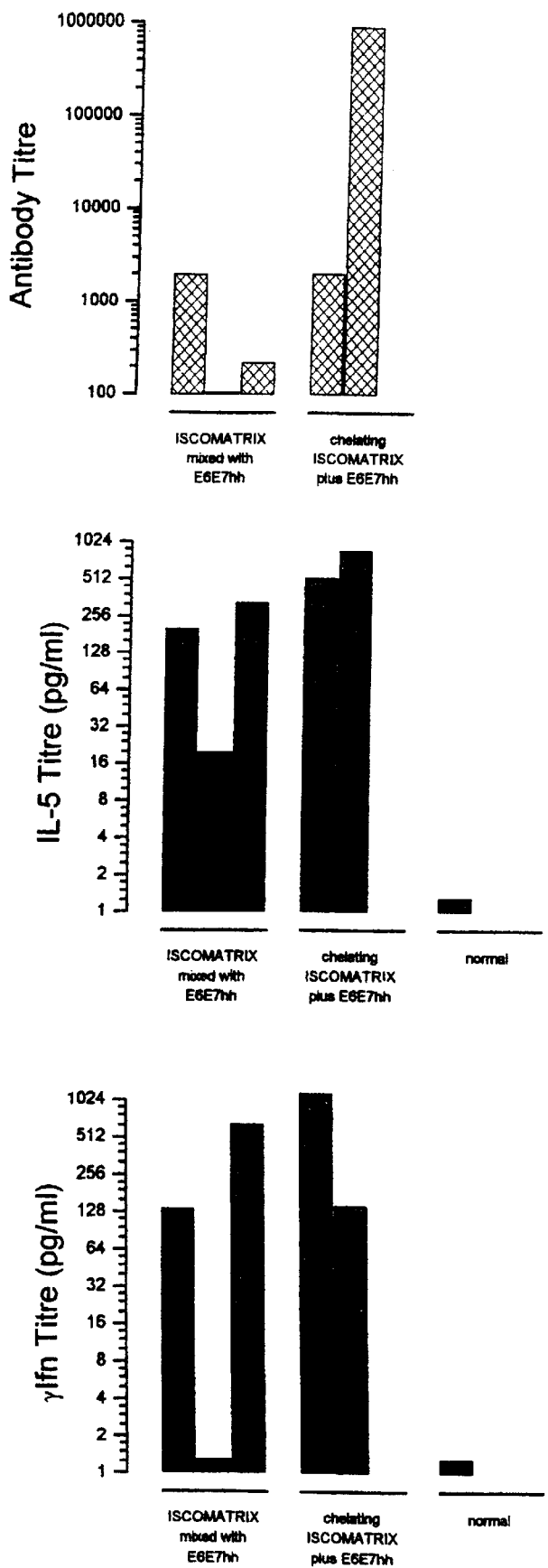
FIG. 4 shows a comparison of ChIMX-E6E7hh and IMX-E6E7hh for A: antibody induction; B: IL-5 induction; and C: γ-IFN induction. Individual bars refer to individual mice.

In order to obtain information regarding the capacity of the formulations to stimulate T-cells that may be important for other aspects of immunity, cytokine levels were measured following in vitro stimulation with E6E7hh. Two×$10^6$ spleen cells were cultured in a volume of 1 ml of RPMI 1640+5% FCS together with 2.5 μg/ml of E6E7hh for 48 hr. The culture supernatants were then assayed for γ-interferon (γifn) and IL-5 by two-site EIAs. Control cultures without antigen indicated that there was no spontaneous production of either cytokine, and cultures with concanavalin A indicated that all spleen cell preparations were capable of producing both IL-5 and yifn. FIG. 4 (middle and lower panels) shows that both the chelating ISCOMATRIX and ISCOMATRIX formulations were effective in priming T-cells to produce IL-5 and γifn, although one of the ISCOMATRIX-vaccinated group produced only IL-5. The fact that both these cytokines were detected indicates that neither formulation exclusively stimulated Th1 or Th2 subpopulations of T-cells, which confirms previous experience with ISCOMATRIX mixed with either E6E7hh or other antigens.

Antibody titres against E7 were measured in an indirect EIA in which GST-E7 (a fusion protein consisting of glutathione-S-transferase and HPV16 E7) was absorbed to wells of a 96-well plate. Following incubation with dilutions of sera, bound antibody was detected by horse radish peroxidase-labelled goat anti-mouse IgG (Kirkegaard & Perry Laboratories Inc., product 074-1802). Titres, expressed as the reciprocal dilution of sera at which the EIA signal was equivalent to the assay background plus 3× the standard deviation, are shown in FIG. 4 (top panel). It is clear that, despite the large variability in titres, both formulations were capable of inducing an antibody response to E7, and that if anything, the chelating ISCOMATRIX formulation was more immunogenic.

The overall conclusion from these studies is that chelating ISCOMATRIX is fully effective as an adjuvant.

EXAMPLE 4

Chelating ISCOMATRIX prepared in Example 1 utilizes the molecule DSIDA to form a link between the particle and the protein. In this example, an alternative compound, DPIDA (1,2-dipalmitoyl-rac-glycerol-3-(8-(3,6-dioxy) octyl-1-amino-N,N-diacetic acid), is used to form chelating ISCOMATRIX. DPIDA has a diacyl C16 tail, whereas DSIDA has a diacyl C18 tail. This was anticipated to improve the solubility characteristics of the chelate compound, such that chelating ISCOMATRIX could be formed without the use of organic solvent.

Similarly to Example 1, ISCOPREP703, cholesterol, and dipalmitoyl phosphatidyl choline (DPPC) were combined in a detergent-containing buffer, and dialysed to form ISCOMATRIX particles typically of 40–60 nm diameter. Chelating ISCOMATRIX was formed in a similar fashion, except that DPIDA and copper were added to the formulation.

In Detail

The following solutions were prepared:

1. 8.49 mg/ml cholesterol, 9.0 mg/ml DPPC, 180 mg/ml Mega-10 in 50 mM bisTRIS, 150 mM NaCl pH 6.9.
2. 8.5 mg/ml cholesterol, 11.3 mg/ml DPIDA, 5.52 mg/Ml $CuCl_2.2H_2O$, 180 mg/ml Mega-10 in 50 mM bisTRIS, 150 mM NaCl pH 6.9.
3. 50 mg/ml ISCOPREP703 in water.

These solutions were combined while mixing in the following order:

Preparation A (ISCOMATRIX) (batch 022A)
1.46 ml 50 mM bisTRIS, 150 mM NaCl pH 6.9
0.205 ml of #1
0.184 ml of #3
Preparation B (chelating ISCOMATRIX) (batch 022B)
4.05 ml 50 mM bisTRIS, 150 mM NaCl pH 6.9
0.38 ml of #1
0.12 ml of #2
0.45 ml of #3

The final composition of the mixtures were:

|  | Preparation A (ISCOMATRIX) batch 022A | Preparation B (chelating ISCOMATRIX) batch 022B |
| --- | --- | --- |
| ISCOPREP703 | 5.0 mg/ml | 4.5 mg/ml |
| cholesterol | 0.94 mg/ml | 0.85 mg/ml |
| DPPC | 1.0 mg/ml | 0.68 mg/ml |
| DPIDA | not added | 0.27 mg/ml |
| $CuCl_2.2H_2O$ | not added | 0.132 mg/ml |
| Mega-10 | 20 mg/ml | 18 mg/ml |

The mixtures were incubated for 2 hr at room temperature, then dialysed against 2 changes of 1 litre of 50 mM bisTRIS, 150 mM NaCl pH 6.9 at room temperature using 10,000 molecular weight cutoff dialysis membrane. This was repeated for an additional 24 hr at 4°.

The preparations were then characterized by photon correlation spectroscopy using a Nicomp370 analyzer, and the mean particle diameter determined following Gaussian analysis of the intensity weighted data. Preparation A (without DPIDA, batch 022A) was 47 nm, and preparation B (with DPIDA, batch 0228) was 49 nm.

In order to demonstrate that the chelating ISCOMATRIX had in fact incorporated copper, and therefore DPIDA, samples of both Preparation A and B were reduced, and cuprous ion was measured using bicinchoninic acid. This assay was a modification of that described by Brenner and Harris (1995).

$CuCl_2.2H_2O$ was dissolved in water at 5865 $\mu$M for use as a standard. A dilution series was prepared in water, and 50 $\mu$l of each dilution or 50 $\mu$l of the test preparations were mixed with 50 $\mu$l of 5 mg/ml sodium ascorbate in a 96 well plate. 100 $\mu$l of bicinchoninic acid solution (Pierce Chemical Company, BCA reagent A) was then added, and the absorbance measured at 562 nm. Using this assay, the value obtained for Preparation B was 205.9 $\mu$M, and that for Preparation A was 30.9 $\mu$M (which was negligible). Clearly, the chelating ISCOMATRIX contains a high level of copper. The figure of 205.9 $\mu$M represents 70.5% of the maximum possible value, assuming that all DPIDA added to the formulation is incorporated into the particles, 100% of chelating sites are occupied by copper, and that the assay used measures chelated copper as efficiently as free copper.

EXAMPLE 5

The use of copper for formation of chelating ISCOMATRIX has several desirable features, notably high affinity binding to proteins with a suitable chelating motif and a toxicity profile indicating suitability for use in vaccines. However, at neutral pH and in aqueous solutions, non-bound copper has the tendency to precipitate as a hydroxide. Phosphate buffers also are not suitable for use with free copper, due to precipitation as copper phosphate. In Example 1 this was controlled by adding the copper to DSIDA in organic solvent in a small excess, and in Example 4 by use of bisTRIS which chelates copper and can buffer the metal in solution. TRIS can also buffer copper by way of chelation, and is more suitable than bisTRIS for pharmaceutical applications since it has already been used as a component of parenteral formulations. In this example, it is shown that ISCOMATRIX can be formed using TRIS-based buffers, and that the copper is protected from precipitation as phosphate once complexed to chelating ISCOMATRIX.

The following solutions were prepared:

1. 200 mg/ml Mega-10, 10 mg/ml cholesterol, 10 mg/ml DPPC, in 150 mM NaCl, 50 mM TRIS, 0.23 mg/ml $CuCl_2.2H_2O$, pH 7.2
2. 200 mg/ml Mega-10, 10 mg/ml cholesterol, 12.6 mg/ml DPIDA in 150 mM NaCl, 50 mM TRIS, 0.23 mg/ml $CuCl_2.2H_2O$, pH 7.2
3. 50 mg/ml ISCOPREP703 in 150 mM NaCl, 50 mM TRIS, 0.23 mg/ml $CuCl_2.2H_2O$, pH 7.2

These solutions were combined while mixing in the following order:

Preparation A (ISCOMATRIX) (batch 033A)
  4.16 ml 50 mM TRIS, 150 mM NaCl, 0.23 mg/ml $CuCl_2.2H_2O$, pH 7.2
  0.416 ml of #1
  0.416 ml of #3
Preparation B (chelating ISCOMATRIX) (batch 033B)
  4.16 ml 50 mM TRIS, 150 mM NaCl, 0.23 mg/ml $CuCl_2.2H_2O$, pH 7.2
  0.316 ml of #1
  0.100 ml of #2
  0.416 ml of #3

The final composition of the mixtures were:

|  | Preparation A (ISCOMATRIX) batch 033A | Preparation B (chelating ISCOMATRIX) batch 033B |
| --- | --- | --- |
| ISCOPREP703 | 4.16 mg/ml | 4.16 mg/ml |
| cholesterol | 0.832 mg/ml | 0.832 mg/ml |
| DPPC | 0.832 mg/ml | 0.632 mg/ml |
| DPIDA | not added | 0.252 mg/ml |
| $CuCl_2.2H_2O$ | 0.23 mg/ml | 0.23 mg/ml |
| Mega-10 | 20 mg/ml | 20 mg/ml |

The mixtures were incubated for 1 hr at room temperature, then dialysed for 16 hr against 1 litre of 50 mM TRIS, 150 mM NaCl pH 7.2 at room temperature using 10,000 molecular weight cutoff dialysis membrane, and then twice for 24 hr against 2 litres of PBS pH 6.9.

The preparations were then analysed using the tests described in Example 4, giving the following results:

Preparation A (batch 033A):
  less than 10 $\mu$M copper
  53 nm diameter
Preparation B (batch 033B):
  247 $\mu$M copper, representing 101% of the theoretical maximum (assuming that all DPIDA added to the formulation is incorporated into the particles, 100% of chelating sites are occupied, and the assay used measures chelated copper as efficiently as free copper).
  67 nm diameter

EXAMPLE 6

The chelating ISCOMATRIX prepared in Example 5 as Preparation B (batch 033B) was evaluated for capacity to bind to a synthetic peptide with sequence (SEQ ID NO: 3): biotin-SGSGKKYKK-beta alanine-HHHHHH-NH2

Figure 5:
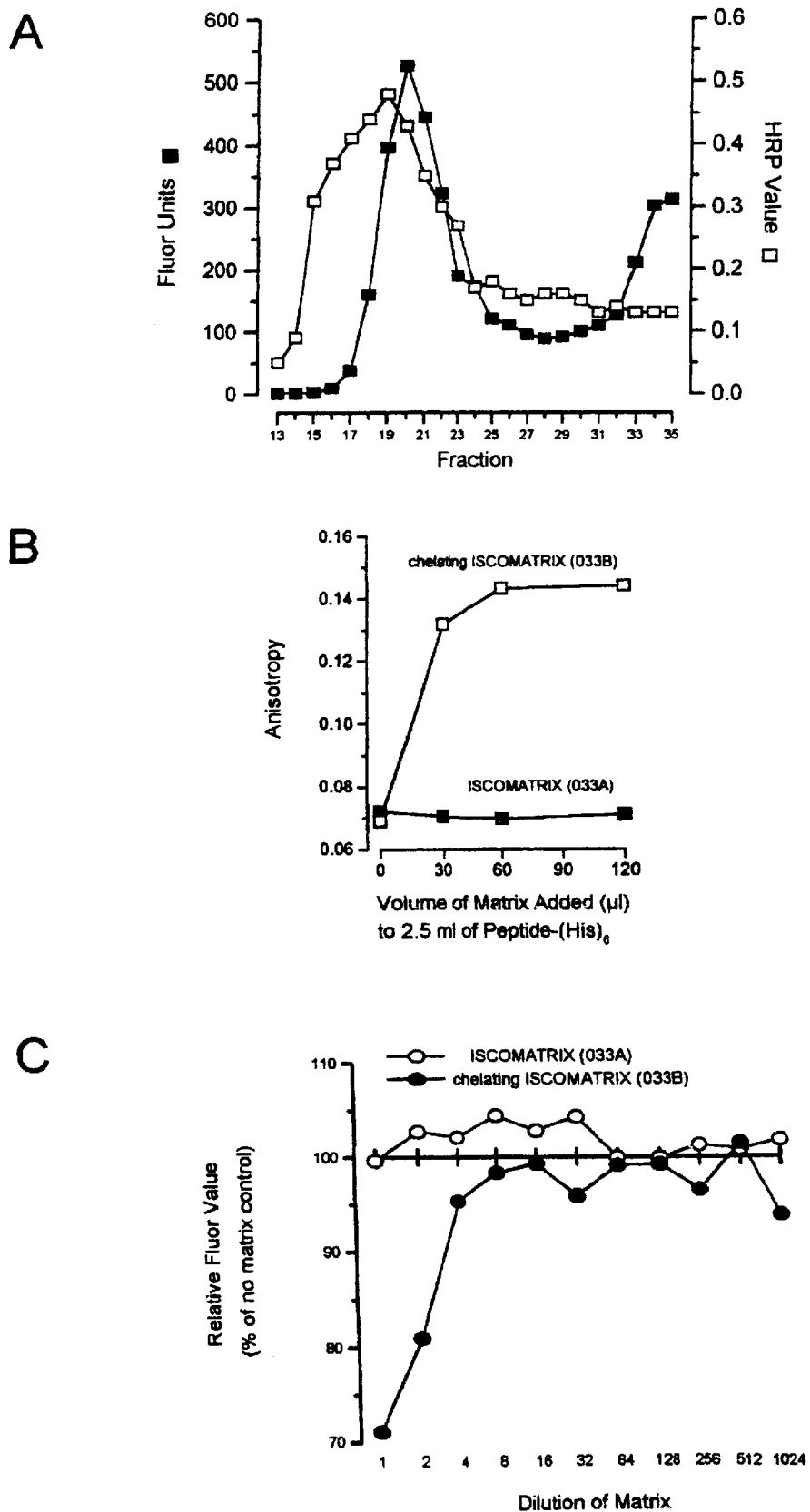
FIG. 5 shows a selection of optimal binding of FITC to peptide by Superdex 30 fractionation. Panel B and C. Demonstration by two techniques that labeled peptide is bound to ChIMX (□ or ○) but not to IMX (■ or ●).

In order to detect binding, the peptide was first reacted with fluorescein isothiocyanate (FITC). The peptide was dissolved in 0.4 ml of 0.1M sodium carbonate, pH 9.5 at 7.5 mg/ml, and then 48 $\mu$l of FITC (at 10 mg/ml in dimethyl sulphoxide) was slowly added while mixing. The reaction was held at room temperature for 3 hr, and then terminated by adding 50 $\mu$l of 3M TRIS, pH 8.2. The labelled peptide was then obtained by size exclusion chromatography on Superdex 30. In order to locate the eluted peptide, individual fractions were assayed for binding to solid phase chelating support (Qiagen 96 well NTA-$Ni^{++}$ immunoassay plates). Binding was detected with peroxidase-labelled streptavidin. This approach was chosen to ensure that the peptide used in binding experiments was intact, and without truncated sequences. FIG. 5 (panel A) shows the elution profile as revealed by this assay, in comparison to direct measurement of fluorescence (bound and unbound). The peptide contains multiple lysine residues, and therefore is likely to be heterogenous with regard to the substitution ratio of fluorescein. A consequence of this is the molecular weight heterogeneity seen in FIG. 5 (panel A). The decrease in fluorescence observed in the high molecular weight species is possibly due to self quenching at high substitution ratio. Fraction 21 was used in binding experiments.

In order to determine whether the fluorescent hexaHIS-containing peptide bound to chelating ISCOMATRIX, fluorescence polarization was used. Peptide was diluted to 284 nM (based on fluorescein content, as measured spectrophotometrically) in 50 mM TRIS, 50 mM sodium phosphate, 150 mM NaCl, pH 6.9. Fluorescence data were acquired from both the horizontal and vertical planes following excitation with polarized light of the peptide solution alone, or following incremental additions of either ISCOMATRIX (Preparation A, Example 5, batch 033A) or chelating ISCOMATRIX (preparation B, Example 5, batch 033B). The results obtained are shown in FIG. 5 (panel B) as anisotropy (α) values, where I(VV) and I(VH) are the fluorescence intensities measured parallel and perpendicular to vertically polarized excitation, respectively, and G is a grating correction factor:

$$\alpha = \frac{I(VV) - I(VH)}{I(VV) + 2GI(VH)}$$

Clearly, the addition of chelating ISCOMATRIX to the peptide has resulted in increased anisotropy values, representing binding to the particles and a consequent reduction in rotational freedom.

Fluorescence polarization measures the ratio of polarized light on two planes, and is therefore independent of the intensity of emitted light. During these measurements, it was noted that the intensity in fact decreased as chelating, but not control, ISCOMATRIX was added to the peptide. This can be accounted for by environmental effects on the quantum yield of the fluorescein label, either directly as a result of binding, or through fluorophor-fluorophor quenching as peptide is concentrated on the surface of the particles.

In order to examine this as an additional indicator of binding, 50 μl of peptide (fraction 21 of fluoresceinated (SEQ ID NO: 3) biotin-SGSGKKYKK-beta alanine-HHHHHH-NH2, as described above) was mixed with 50 ul of dilutions either ISCOMATRIX (Preparation A, Example 5, batch 033A) or chelating ISCOMATRIX (preparation B, Example 5, batch 033B) in wells of a microtiter place. Final ligand concentration was 1.3 μM (based on fluorescein content, as measured spectrophotometrically), and all dilutions were in 50 mM TRIS, 50 mM sodium phosphate, 150 mM NaCl, pH 6.9. Fluorescence was then measured using a Fluoroskan II vertical beam fluorospectrophotometer, at excitation and emission wavelengths of 355 nm and 460 nm, respectively.

FIG. 5 (panel C) clearly shows that chelating, but not control, ISCOMATRIX quenches the fluorescence signal of the labelled (SEQ ID NO: 4) (his)$_6$-containing peptide.

EXAMPLE 7

Chelating ISCOMATRIX was shown to bind the recombinant molecule E6E7hh in Example 2. In order to further examine the properties of chelating ISCOMATRIX with bound protein the control ISCOMATRIX made in Example 5 (batch 033A), and the chelating ISCOMATRIX preparation made in Examples 4 (batch 022B) and 5 (batch 033B) were analysed for binding to two different (SEQ ID NO: 4) (His)$_6$-containing proteins: E6E7hh and Family C protein of *Helicobacter pylori* (HpFC). HpFC was prepared from *E. coli* inclusion bodies by IMAC, followed by exhaustive dialysis against PBS, pH 7(a)2. As expressed, HpFC is a 131 amino acid residue protein of approximately 14,100 MW, includes a C-terminal (SEQ ID NO: 4) (His)$_6$ tag, and has primary amino acid sequence:

MAISKEEVLEYIGSLSVLELSELVKM-FEEKFGVSATPTVVAGAAVAGGAAAE SEEKTEFNVILADSGAEKIKVIKVVRE-ITGLGLKEAKDATEKTPHVLKEGVNKEEAETIK KKLEEVGAKVEVKHHHHHH (SEQ ID No. 2)

In these reactions 50 μg of protein was mixed with 400 μg of ISCOMATRIX (based on ISCOPREP703 content), and after 1 hr the apparent size of the particles was measured. The final reaction buffer varied according to the buffer components of the individual reactants, and is shown in Table 1. For all reactions, the pH was 6.9–7.5. The reactions with E6E7hh were carried out in 4M urea in order to prevent precipitation of the protein, whereas those with HpFC were carried out in the absence of denaturant.

Table 1 shows that the two preparations of chelating ISCOMATRIX behaved completely differently with respect to the physical properties of the complexes formed on addition of (SEQ IDNO: 4) (His)$_6$-containing protein. Batch 033B formed complexes of large size with both HpFC (in the absence of urea) and E6E7hh (in 4M urea), whereas batch 022B formed complexes with E6E7hh that represented a comparatively moderate size increase.

The major difference between batches 022B and 033B of chelating ISCOMATRIX was the procedure for preparation, and in particular, the buffer components in the final formulation. In order to determine whether this affected the type of complexes formed with (SEQ ID NO: 4) (His)$_6$-containing proteins, a cross-dialysis experiment was performed. As shown in Table 2, batch 022B was dialysed out of 50 mM bisTRIS, 150 mM NaCl, pH 6.9 and into either PBS, TRIS, or bisTRIS buffers (as specified in Table 2), and batch 033B was dialysed out of PBS, pH 6.9 and into the same three buffers. The dialysed chelating ISCOMATRIX preparations were then reacted with E6E7hh and increases in size evaluated.

It can be seen that dialysis of batch 033B chelating ISCOMATRIX into either bisTRIS or TRIS buffers had a dramatic reductive effect on the size of the complexes formed with E6E7hh, when compared with the same preparation maintained in PBS. In contrast, 022B chelating ISCOMATRIX formed complexes of similar size irrespective of the buffer.

Operationally, this shows that the size of the protein-ISCOMATRIX complexes formed with (His)$_6$-containing protein can be controlled by manipulating the buffer components in the formulation, and that bisTRIS and TRIS are particularly beneficial in this regard. This is most easily explained by the capacity of these buffers to bind copper. Published association values are:

$\log K_{Cu \ldots TRIS}{}^{Cu}$=4.05 Fischer, et al. (1979).

$\log K_{Cu \ldots bisTRIS}{}^{Cu}$=5.27 Scheller, et al. (1989).

One explanation for this effect is that the increase in complex size is due to crosslinking through secondary metal binding sites on the protein, resulting in particle-aggregation. Chelating agents with weak to moderate affinity to copper may be able to block such secondary interactions. This is also consistent with the finding that 022B chelating ISCOMATRIX, dialysed out of bisTRIS into PBS, did not form complexes of large size. In this case it can be expected that, under the dialysis conditions employed, bisTRIS would not have been removed completely from the ISCOMATRIX by virtue of its affinity for copper bound to DPIDA.

TABLE 1

Variation in Size of Protein Complexes formed by chelating ISCOMATRIX Preparations

| Preparation | Size before addition of protein | Reaction conditions | Size after addition of protein |
|---|---|---|---|
| ISCOMATRIX batch 022A in 50 mM bisTRIS, 150 mM NaCl pH 6.9 | 47 ± 4 nm | | ND |
| chelating ISCOMATRIX batch 022B in 50 mM bisTRIS, 150 mM NaCl pH 6.9 | 49 ± 9 nm | 50 μg/ml E6E7hh 4M urea 5 mM TRIS 10 mM bisTRIS 280 mM NaCl | 112 ± 47 |
| ISCOMATRIX batch 033A in PBS pH 6.9 | 53 ± 14 nm | 50 μg/ml E6E7hh 4M urea 5 mM TRIS 2 mM Na phosphate 280 mM NaCl | 65 ± 27 |
| chelating ISCOMATRIX batch 033B in PBS pH 6.9 | 67 ± 33 nm | 50 μg/ml E6E7hh 4M urea 5 mM TRIS 2 mM Na phosphate 280 mM NaCl | 300,000 |
| ISCOMATRIX batch 033A in PBS pH 6.9 | 53 ± 14 nm | 50 μg/ml HpFC 10 mM Na phosphate 150 mM NaCl | 59 ± 33 |
| chelating ISCOMATRIX batch 033B in PBS pH 6.9 | 67 ± 33 nm | 50 μg/ml HpFC 10 mM Na phosphate 150 mM NaCl | 1100 |

TABLE 2

Effect of Buffer in Cross-Dialysis Experiment

| Preparation | → New Buffer | → Size | Protein added* | → Size |
|---|---|---|---|---|
| chelating ISCOMATRIX batch 022B in 50 mM bisTRIS, 150 mM NaCl, pH 6.9 49 nm | PBS, pH 6.9 | 48 nm | 50 μg/ml E6E7hh | 124 nm |
| | 50 mM bisTRIS 150 mM NaCl, pH 6.9 | 48 nm | 50 μg/ml E6E7hh | 130 nm |
| | 50 mM TRIS 150 mM NaCl, pH 7.2 | 48 nm | 50 μg/ml E6E7hh | 116 nm |
| chelating ISCOMATRIX batch 033B in PBS, pH 6.9 67 nm | PBS, pH 6.9 | 71 nm | 50 μg/ml E6E7hh | 5300 nm |
| | 50 mM bisTRIS 150 mM NaCl, pH 6.9 | 55 nm | 50 μg/ml E6E7hh | 202 nm |
| | 50 mM TRIS 150 mM NaCl, pH 7.2 | 60 nm | 50 μg/ml E6E7hh | 172 nm |

*Reaction conditions were matrix in buffers as shown in Table, plus an equal volume of 100 μg/ml E6E7hh in 10 mM TRIS, 0.5M NaCl, 50 mM Na phosphate, pH 7.5. Samples were held at room temperature for 1 hr prior to analysis of size distributions.

EXAMPLE 8

In this Example it is shown that the amount of protein is an additional variable that influences complex size. ISCOMATRIX and chelating ISCOMATRIX were prepared as follows:

The following solutions were prepared:
1. 200 mg/ml Mega-10, 10 mg/ml cholesterol, 10 mg/ml DPPC, in 150 mM NaCl, 50 mM bisTRIS, pH 6.9
2. 200 mg/ml Mega-10, 10 mg/ml cholesterol, 12.6 mg/ml DPIDA in 150 mM NaCl, 50 mM bisTRIS, 0.23 mg/ml $CuCl_2.2H_2O$, pH 6.9
3. 50 mg/ml ISCOPREP703 in 150 mM NaCl, 50 mM bisTRIS, pH 6.9.

These solutions were combined while mixing in the following order:

Preparation A (ISCOMATRIX) (batches 040-2m,040-3m)
  0.8 ml 50 mM bisTRIS, 150 mM NaCl, 0.29 mg/ml $CuCl_2.2H_2O$, pH 6.9
  0.1 ml of #1
  0.1 ml of #3

Preparation B (chelating ISCOMATRIX) (batches 040-2c,040-3c)
  0.8 ml 50 mM bisTRIS, 150 mM NaCl, 0.29 mg/ml $CuCl_2.2H_2O$, pH 6.9
  0.076 ml of #1
  0.024 ml of #2
  0.1 ml of #3

The final composition of the mixtures were:

| | Preparation A (ISCOMATRIX) batch 040-2m batch 040-3m | Preparation B (chelating ISCOMATRIX) batch 040-2c batch 040-3c |
|---|---|---|
| ISCOPREP703 | 5 mg/ml | 5 mg/ml |
| cholesterol | 1 mg/ml | 1 mg/ml |

-continued

|  | Preparation A (ISCOMATRIX) batch 040-2m batch 040-3m | Preparation B (chelating ISCOMATRIX) batch 040-2c batch 040-3c |
|---|---|---|
| DPPC | 1 mg/ml | 0.76 mg/ml |
| DPIDA | not added | 0.30 mg/ml |
| CuCl$_2$.2H$_2$O | 0.23 mg/ml | 0.23 mg/ml |
| Mega-10 | 20 mg/ml | 20 mg/ml |

The mixtures were incubated for 1 hr at room temperature, then dialysed for 16 hr at room temperature using 10,000 molecular weight cutoff dialysis membrane against either 1 liter of 50 mM bisTRIS, 150 mM NaCl, pH 6.9 (batch 040-2m, batch 040-2c) or 1 liter of 50 mM bisTRIS, 150 mM NaCl, 0.23 mg/ml CuCl$_2$.2H$_2$O, pH 6.9 (batch 040-3m, batch 040-3c). All preparations were then dialysed for 8 hr against 500 ml of 50 mM sodium phosphate, 50 mM TRIS, 150 mM NaCl, pH 6.9, and then for 48 hr against 500 ml of 50 mM sodium phosphate, 50 mM TRIS, 150 mM NaCl, pH 6.9. Batches 040-2m and 040-3m of ISCOMATRIX, and 040-2c and 040-3c of chelating ISCOMATRIX differed only according to the presence of copper in the first dialysis buffer.

The preparations were then analysed using the tests described in Example 4.

For batch 040-2m of ISCOMATRIX: 16 $\mu$M copper, 52 nm diameter

For batch 040-3m of ISCOMATRIX: 17 $\mu$M copper, 52 nm diameter

For batch 040-2c of chelating ISCOMATRIX: 220 $\mu$M copper, 64 nm diameter

For batch 040-3c of chelating ISCOMATRIX: 220 $\mu$M copper, 62 nm diameter

Figure 6:
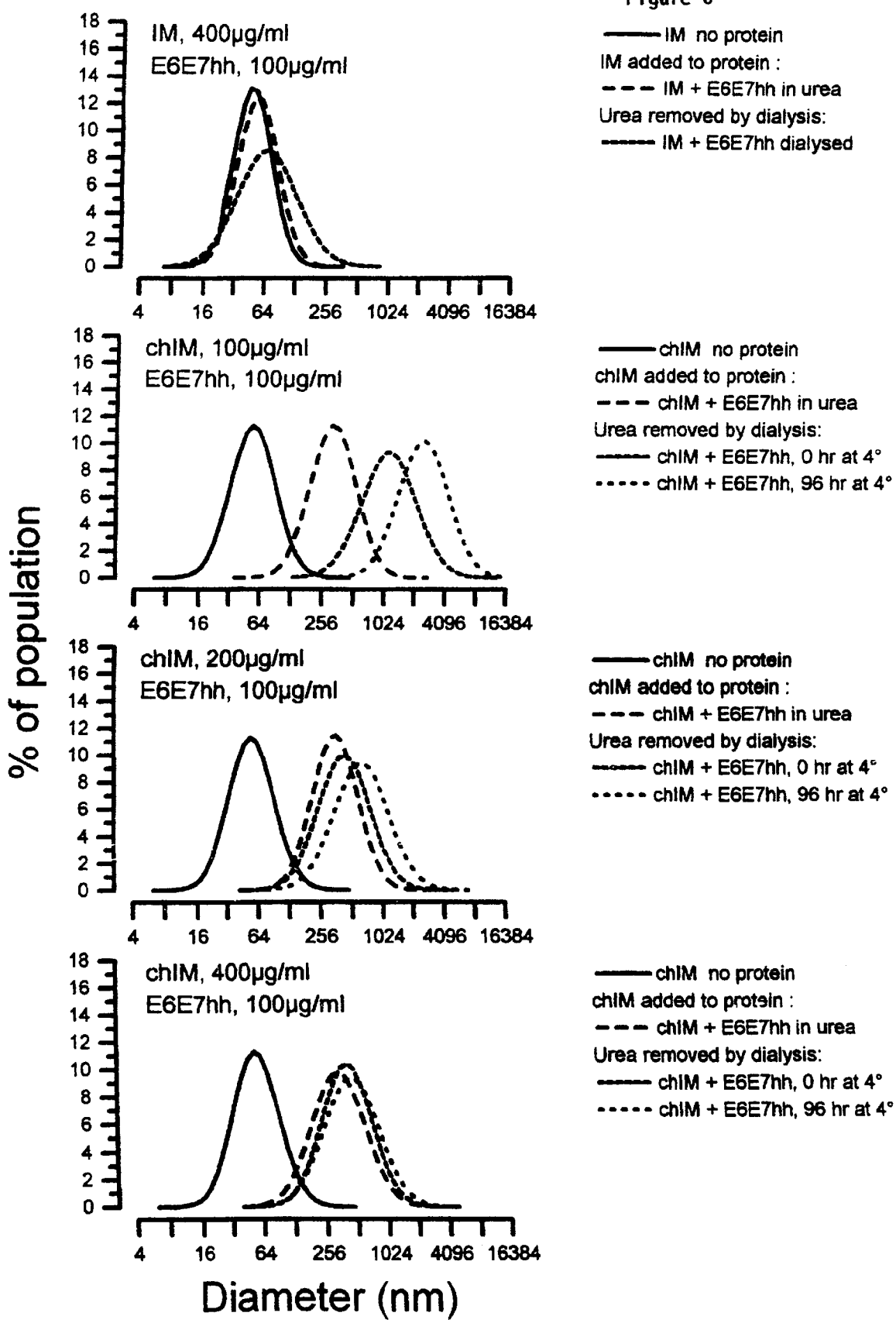
FIG. 6 demonstrates the effect on matrix particle size of E6E7hh and A: IMX, B: ChIMX at 1:1 protein matrix, C: ChIMX at 1:2 and D: ChIMX at 1:4. —— No protein; --- E6E7hh in urea; ——— E6E7hh, urea dialyzed; ···· E6E7hh, urea dialyzed and stored 96 h 4° C.

In order to analyze the changes following combination of chelating ISCOMATRIX with protein, various amounts of ISCOMATRIX (pooled batches 040-2m and 040-3m) or chelating ISCOMATRIX (pooled batches 040-2c and 040-3c) were added to 100 $\mu$g of E6E7hh, to give a formulation containing 4M urea, 50 mm TRIS, 50 mM sodium phosphate, 150 mM NaCl, pH 6.9. After 1 hr at room temperature, the size distributions were measured. The urea was then removed from the formulations by dialysis against 50 mm TRIS, 50 mM sodium phosphate, 150 mM NaCl, pH 6.9 buffer, and the size distributions measured again both immediately following dialysis and after storage at 4° for 96 hr. FIG. 6 shows that ISCOMATRIX added to E6E7hh had no effect on the size distribution of particles, but that there were marked changes in the case of chelating ISCOMATRIX. Furthermore, the size distribution of chelating ISCOMATRIX plus E6E7hh was dependent on the ratio of protein to matrix (expressed as $\mu$g/ml of ISCOPREP703). At high levels of protein (1:1 ratio), larger complexes formed and the size of the complexes increased with time. In contrast, at low levels of protein (1:4) stable complexes of moderate size were observed.

It can be concluded that the level of protein is an important determinant of both complex size and stability, and that at a ratio of 100 $\mu$g of E6E7hh to 400 $\mu$g/ml of ISCOPREP703, a stable well defined formulation can be achieved. This is well within the range expected to result in efficacious vaccine formulations.

EXAMPLE 9

In order to demonstrate the generality of chelating ISCOMATRIX for the formulation of vaccines using a variety of antigens, the binding of an additional (His)$_6$-containing protein was examined. The chelating ISCOMATRIX used in this study was prepared by the methodology developed in preceding examples.

The following solutions were prepared:
1. 200 mg/ml Mega-10, 10 mg/ml cholesterol, 10 mg/ml DPPC, in 150 mM NaCl, 50 mM TRIS, 0.6 mM CUCl$_2$.2H$_2$O, pH 7.2
2. 200 mg/ml Mega-10, 10 mg/ml cholesterol, 9 mg/ml DPPC, 1.26 mg/nl DPIDA in 150 mM NaCl, 50 mM TRIS, 0.6 mM CuCl$_2$.2H$_2$O, pH 7.2
3. 50 mg/ml ISCOPREP703 in 150 mM NaCl, 50 mM TRIS, pH 7.2

These solutions were combined while mixing in the following order:

Preparation A (ISCOMATRIX) (batch M-1207)
8 ml 50 mM TRIS, 150 mM NaCl, 0.6 mM CuCl$_2$.2H$_2$O, pH 7.2
1 ml of #1
1 ml of #3

Preparation B (chelating ISCOMATRIX) (batch ch10-1207)
8 ml 50 mM TRIS, 150 mM NaCl, 0.6 mM CuCl$_2$.2H$_2$O, pH 7.2
1 ml of #2
1 ml of #3

The final composition of the mixtures were:

|  | Preparation A (ISCOMATRIX) batch M-1207 | Preparation B (chelating ISCOMATRIX) batch ch10-1207 |
|---|---|---|
| ISCOPREP703 | 5 mg/ml | 5 mg/ml |
| Cholesterol | 1 mg/ml | 1 mg/ml |
| DPPC | 1 mg/ml | 0.9 mg/ml |
| DPIDA | not added | 0.126 mg/ml |
| CuCl$_2$.2H$_2$O | 5.4 mM | 5.4 mM |
| Mega-10 | 20 mg/ml | 20 mg/ml |

The mixtures were incubated for 90 min at room temperature, then dialysed for 16 hr against 2 liters of 50 mM TRIS, 150 mM NaCl pH 7.2 at room temperature using 12,000 molecular weight cutoff dialysis membrane, and then twice for 24 hr at 4° against 2 liters of 50 mM TRIS, 50 mM sodium phosphate, 150 mM NaCl, pH 6.9. The preparations were then sterilized by filtration through a 0.22 $\mu$M membrane. The particles formed showed the "soccer ball" morphology that is characteristic of ISCOMs when observed by electron microscopy. Size distributions and copper analysis also demonstrated the successful formation of chelating ISCOMATRIX:

Preparation A (batch M-1207):
less than 10 $\mu$M copper
60 nm diameter

Figure 7:
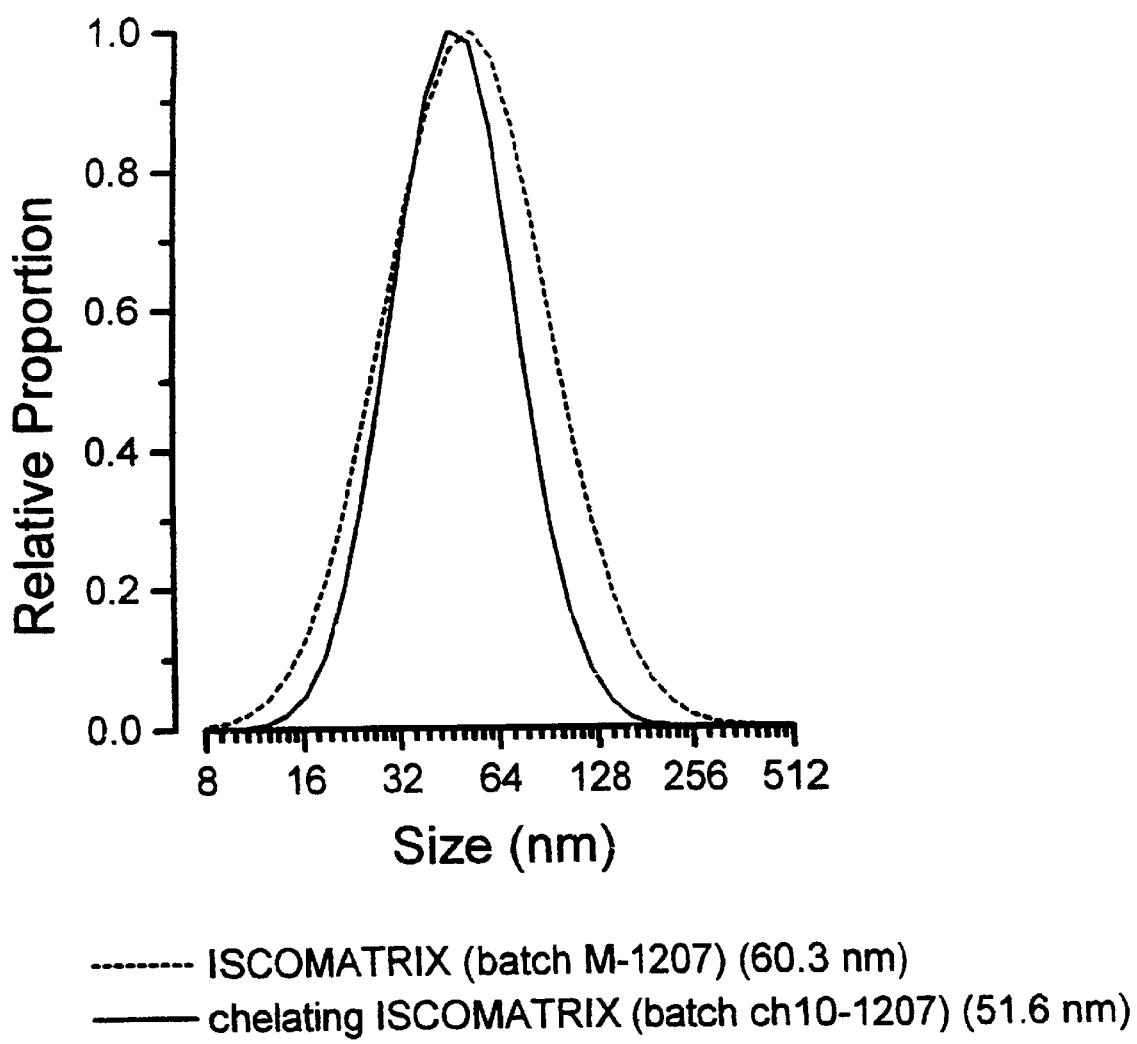
FIG. 7 shows the size distribution of IMX ----- and ChIMX —— particles.

Preparation B (batch ch10-1207):
101 $\mu$M copper, representing 80% of the theoretical maximum (assuming that all DPIDA added to the formulation is incorporated into the particles, 100% of chelating sites are occupied, and the assay used measures chelated copper as efficiently as free copper).
52 nm diameter The size distributions of Preparations A and B are shown as FIG. 7.

In order to demonstrate the capacity of chelating ISCOMATRIX to bind to a (His)$_6$-containing protein other than E6E7hh, and thereby establish the generality of the binding mechanism, Family C protein of *Helicobacter pylori* (HpFC) (as described in Example 7) was used.

Fifty μg of HpFC in PBS, pH 7.2 was mixed with 400 μg (based on ISCOPREP703 content) of ISCOMATRIX (batch M-1207), chelating ISCOMATRIX (batch ch10-1207), or chelating ISCOMATRIX (batch ch10-1207) in the presence of 250 mM imidazole. The mixtures were incubated for 1 hr, and then applied to the top of a 20–60% w/w gradient of sucrose in 50 mM TRIS, 50 mM sodium phosphate, 150 mM NaCl, pH 6.9, and centrifuged at 35,000 rpm for 15 hr in a Beckman SW40 rotor. Individual fractions were collected and assayed using the following procedures:

1. For ISCOMATRIX, the increase in quantum yield of the fluorescent probe diphenylhexatriene (DPH) on transfer from the aqueous phase to the lipophilic ISCO-MATRIX environment was measured using the procedure detailed in Example 2.

2. To measure the amount of HpFC associated with ISCOMATRIX, a two site EIA was used. Aliquots of each fraction were added to wells of a microtiter plate coated with monoclonal antibody GP2.3C9.1C5 (specific for HpFC). Following a series of washes and incubations, bound HpFC associated with ISCOMA-TRIX was detected with a second monoclonal antibody (DD15.5G11), which had been chemically conjugated with the enzyme horse radish peroxidase (HRP). This Mab is specific for an epitope of Quillaia saponin present both in the crude QuilA (QA) fraction and the highly purified ISCOPREP703 material derived from it, and detectable on the surface of ISCOMATRIX. The amount of enzymic activity of HRP remaining in the microtiter plate following additional washes and incubations is indicative of the amount of HpFC associated with ISCOMATRIX. This is conveniently measured by a color change following incubation with a substrate of HRP.

3. The total amount of HpFC was measured by a qualitative direct EIA. Sucrose gradient fractions were diluted 1 in 20 in 50 mM sodium carbonate pH 9.5, absorbed to wells of immunoassay plates, and then the bound HpFC detected by means of a peroxidase-labelled Mab specific for HpFC (GP2.3C9.1C5). This assay design does not provide quantitative data, and was adopted because only one reagent specific for HpFC was available.

4. The total amount of (SEQ ID NO: 4) $(His)_6$-containing protein was measured by a qualitative indirect EIA. Sucrose gradient fractions were diluted 1 in 20 in 50 mM sodium carbonate pH 9.5, absorbed to wells of immunoassay plates, and then the bound $(His)_6$-containing protein detected by means of a Mab specific for (SEQ ID NO: 4) $(His)_6$ (Dianova Gmb, product HDIA-900) and peroxidase-labelled goat anti-mouse IgG (Kirkegaard & Perry Laboratories Inc., product 074-1802). This assay design does not provide quantitative data.

Figure 8:
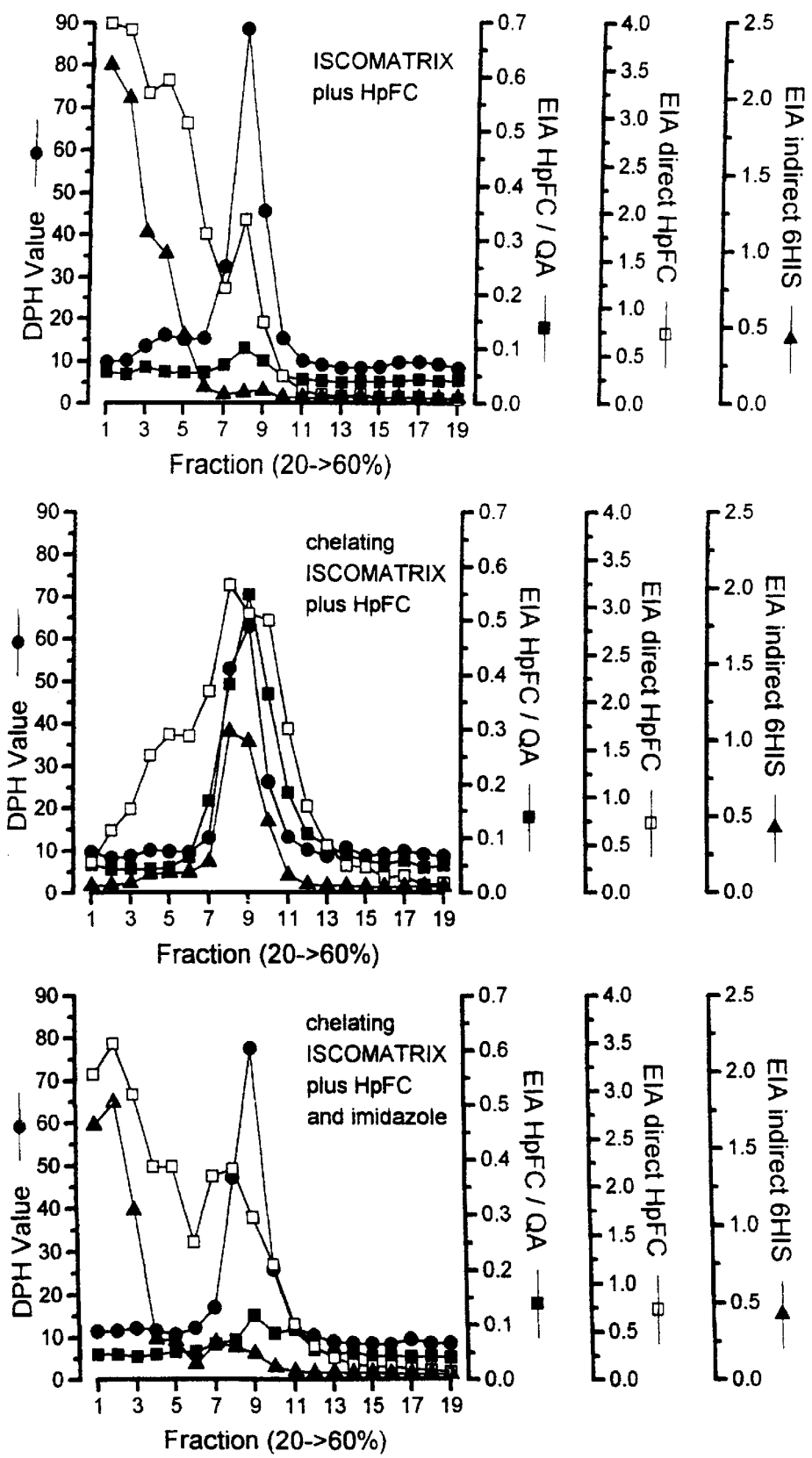
FIG. 8 shows the analysis of sucrose gradient fractions of H. pylori Chh mixed with A: IMX, B: ChIMX and C: ChIMX plus imidazole. ● matrix; ○ H. pylori C associated with matrix; □ Total H. pylori C by protein EIA; ▲ Total H. pylori C by hh EIA.

FIG. 8 shows the analysis of sucrose gradient fractions by these four assays. For all three preparations, there is a single well defined chISCOMATRIX or ISCOMATRIX peak centered on fractions 8–10. In the formulation of chISCOMA-TRIX plus HpFC, there is a clear association of HpFC with the chISCOMATRIX, as revealed by the coincidence of the total HpFC (direct HpFC), the total (SEQ ID NO: 4) $(His)_6$-containing protein (indirect (SEQ ID NO: 4)6HIS), and the ISCOMATRIX-associated HpFC (HpFC/QA). Not all of the HpFC protein bound to chISCOMATRIX since there was substantial total HpFC present in fractions without chISCOMATRIX, however (SEQ ID NO: 4) $(His)_6$ could not be detected in these fractions. Thus some of the HpFC does not have (SEQ ID NO: 4) $(His)_6$ sterically available for antibody-binding, and (not surprisingly) this material is also unable to bind to chISCOMATRIX. The profiles of the control formulations were markedly different. For both ISCOMATRIX plus HpFC and chISCOMARIX plus HpFC in the presence of imidazole, there was very little HpFC present in the fractions containing ISCOMATRIX, and ISCOMATRIX-associated HpFC (Hpy-C/QA) was virtually undetectable. All of the (SEQ ID NO: 4) $(His)_6$-containing protein was towards the top of the gradient.

This analysis provides clear evidence of binding of HpFC to chelating ISCOMATRIX, and of the importance of chelation as the binding mechanism.

EXAMPLE 10

The two most important properties of a vaccine formulation are that is immunogenic, and has an acceptable toxicity profile. To determine whether ormulations based on chelating ISCOMATRIX fulfilled these criteria, a rabbit immunisation trial was performed in which both the serological response to E6E7hh and local toxicity was evaluated. Vaccine formulations were as follows:

|  | chelating ISCOMATRIX | ISCOMATRIX |
|---|---|---|
| ISCOPREP703 | 200 μg/ml | 200 μg/ml |
| E6E7hh | 200 μg/ml | 200 μg/ml |
| Urea | 1.6 M | 4 M |
| TRIS | 42 mM | 11.0 mM |
| NaCl | 0.22 M | 0.43 M |
| sodium phosphate | 50 mM | 42 mM |
| pH | 6.9 | 7.5 |

All buffers were prepared free from preservative and sterile-filtered. Chelating ISCOMATRIX batch 033B (Example 8) and ISCOMATRIX batch 055223748 (clinical grade material, CSL Ltd) were used for vaccine formulation.

All rabbits received 0.5 ml of vaccine formulation intramuscularly. The first dose was in the right hind leg, and the second in the left hind leg. On the day prior to dosing, the sites were shaved with clippers and fine hair removed using depilating cream (Neplisoap-Cosmex International. The sites did not show signs of irritation, cuts, abrasions, lumps or any other visual marks or palpable lumps. Injection was by a 26G neeedle, and dose levels were 100 μg of ISCO-PREP703 (as either ISCOMATRIX or chelating ISCOMATRIX) and 100 μg of E6E7hh, or diluent only. The dosing/bleeding schedule was: day −1 (pre-bleed and 1° dose site preparation); day 0 (1° dose); day 6 (2° dose site preparation); day 7 (bleed, then 2° dose); day 14 (bleed, then biopsy 2° dose site).

To monitor local reactions, the sites were examined at 4 hr post-injection and then daily by two independent observers, of whom one did not have access to the coding of the experimental animals. At the completion of the study, biopsies from the site of the second dose were examined for histological abnormalities. Based on a score of 0 to 5 (where 0=no reaction., 1=small area of reddening, 2=raised flat area with large area of reddening, 3=soft lump with very large area of reddening, 4=hard lump, 5=abscess), all dose sites were rated 0 by both observers at all time points. The biopsies were evaluated as histologically normal.

To monitor serological responses, sera were assayed by EIA for antibodies against either E6E7hh or GST-E7 (a fusion protein consisting of glutathione-S-tranferase and E7). The results are shown below in Table 3. It can be seen that both chelating ISCOMATRIX with E6E7hh and ISCOMATRIX plus E6E7hh induced a strong specific antibody response, which could be detected against both GST-E7 and E6E7hh.

TABLE 3

|  | chlSCOMATRIX E6E7hh | | ISCOMATRIX E6E7hh | | Diluent Control | |
| --- | --- | --- | --- | --- | --- | --- |
|  | Rabbit 940 | Rabbit 941 | Rabbit 910 | Rabbit 915 | Rabbit 919 | Rabbit 920 |
| Prebleed (assay vs GST-E7) | 3.0 | 3.0 | 3.1 | 3.1 | 3.0 | 2.6 |
| Post-2° bleed (assay vs GST-E7) | 5.8 | 5.7 | 5.8 | 6.0 | ND | ND |
| Prebleed (assay vs E6E7hh) | 2.7 | 2.7 | 3.6 | 3.1 | 2.6 | 2.7 |
| Post-2° bleed (assay vs E6E7hh) | 5.9 | 5.8 | 6.0 | 6.1 | ND | ND |

Titres are expressed as Log 10 reciprocal dilutions of sera giving an EIA signal equivalent to assay background plus 3 times the standard deviation.

EXAMPLE 11

To further examine the stability of E6E7hh vaccine formulations with chelating ISCOMATRIX, the physical properties of the complexes were evaluated over time at two different temperatures, and at three different ratios of protein to ISCOPREP703. For this analysis the apparent size of the complexes (as measured by photon correlation spectroscopy) and the association of protein (as measured by assay of sucrose gradient fractions) was evaluated.

Chelating ISCOMATRIX batch ch10-1207 (preparation described in Example 9) was used. In order to accurately measure E6E7hh in a variety of valencies and physical states, the formulations included protein that had been labelled with tritium using N-succinimidyl [2,3-$^3$H] propionate. To label E6E7hh with this reagent in the absence of urea, the reaction was performed with E6E7hh bound to an IMAC resin (Qiagen Ni-NTA Superflow) in 0.1M sodium phosphate, 0.2M NaCl, pH 8.0. This also had the advantage of protecting the (SEQ ID NO: 4) (His)$_6$ sequence. Once labelled, the solid phase was extensively washed with 8M urea, 0.1M sodium phosphate, 10 mM TRIS, 0.3M NaCl, pH 8.0, and the protein then eluted with the same buffer adjusted to pH 4.4. In order to ensure that the labelled protein was free of low MW reaction components and Ni derived from the solid phase (which could possibly interfere with binding to chelating ISCOMATRIX), the material was dialysed against 8M urea, 50 mM sodium phosphate, 50 mM TRIS, 150 mM NaCl, 10 mM EDTA, pH 4.0 at 4° for 16 hr, and then against 8M urea, 50 mM sodium phosphate, 50 mM TRIS, 150 mM NaCl, pH 6.9. Recovered material was measured to be 370 µg/ml by the Coomassie Plus assay (Pierce Chemical Company) using the original E6E7hh preparation (quantitated by amino acid analysis) as a standard. Specific activity of the labelled protein was 925 CPM/µg.

The formulations tested were prepared as follows:

| Component | Formulations (µg ISCOPREP703/µg E6E7hh) | | |
| --- | --- | --- | --- |
|  | 1400/125 | 1400/250 | 1400/500 |
| 8M urea, 50 mM sodium phosphate, 50 mM TRIS, 150 mM NaCl, pH 6.9 | 1045 µl | 855 µl | 478 µl |
| unlabelled E6E7hh in 8M urea, 50 mM sodium phosphate, 50 mM TRIS, 150 mM NaCl, pH 6.9 | 185 µl (305 µg) | 375 µl (617 µg) | 752 µl (1242 µg) |
| [$^3$H] E6E7hh in 8M urea, 50 mM sodium phosphate, 50 mM TRIS, 150 mM NaCl, pH 6.9 | 20 µl (7.5 µg) | 20 µl (7.5 µg) | 20 µl (7.5 µg) |
| chelating ISCOMATRIX in 50 mM sodium phosphate, 50 mM TRIS, 150 mM NaCl, pH 6.9 | 1250 µl (3500 µg) | 1250 µl (3500 µg) | 1250 µl (3500 µg) |
| CPM/20 µl (measured) | 458 | 592 | 503 |
| CPM/µg (calculated) | 183 | 118 | 50 |

The preparations were incubated for 60 min at room temperature, then initial measurements of the size distribution of the complexes (in 4M urea) were taken. After dialysis for 16 hr at 4° against 50 mM sodium phosphate, 50 mM TRIS, 150 mM NaCl, 0.5% 2-phenoxyethanol, pH 6.9, the formulations were diluted in the same buffer to 318 µg/ml of ISCOPREP703, and aliquoted at 0.6 ml in glass containers for storage at either 4° or 31°. Through the course of the study, measured mean recovery was 87% for ISCOPREP703 (15 determinations by reverse phase HPLC), and for E6E7hh recovered as tritium; 96.1% (1400/125 formulation—5 determinations), 70.0% (1400/250 formulation—5 determinations), and 84.3% (1400/500 formulation—5 determinations).

At various times, samples were assayed for size distribution by photon correlation spectroscopy to indicate gross changes in particle physical properties. To indicate fine differences in the composition of the particles, samples were fractionated by density gradient centrifugation. Six hundred µl of each formulation was applied to the top of a 20–60% w/v linear gradient of sucrose in 50 mM sodium phosphate, 50 mM TRIS, 150 mM NaCl, 0.5% 2-phenoxyethanol, pH 6.9, and centrifuged in an SW40 rotor for 17 hr at 40°. Individual fractions were then assayed for:

1. E6E7hh content by EIA. Fractions were diluted 1 in 10, and added to wells of a microtiter plate coated with monoclonal antibody LHIL-16E76D (specific for HPV16 E7). Following a series of washes and incubations, bound HPV 16 E7 was detected with a second monoclonal antibody (LHIL-16E78F, specific for HPV16 E7) which had been chemically conjugated with the enzyme horse radish peroxidase (HRP). HRP remaining in the microtiter plate following additional washes and incubations was measured by a color change following incubation with a substrate of HRP.

2. E6E7hh associated with chelating ISCOMATRIX by EIA. Fractions were diluted 1 in 10, and added to wells of a microtiter plate coated with monoclonal antibody LHIL-16E76D (specific for HPV16 E7). Following a series of washes and incubations, bound HPV16 E6E7hh associated with ISCOMATRIX was detected with a second monoclonal antibody (DD1 5.5G11, specific for an epitope of Quillaia saponin detectable on the surface of ISCOMATRIX), which had been chemically conjugated with the HRP. HRP remaining in the microtiter plate following additional washes and incubations was measured by a color change following incubation with a substrate of HRP.

3. E6E7hh by radioactive content. 100 $\mu$l of each fraction was diluted with 200 $\mu$l of water, emulsified with 1.2 ml of Packard Insta-Gel (product 6013009), and counts per minute determined using a $\beta$-scintillation spectrometer.

4. ISCOMATRIX was measured using the fluorescent probe diphenylhexatriene (DPH). On transfer from the aqueous phase to the lipophilic ISCOMATRIX, DPH undergoes an increase in quantum yield, which was measured using a Fluoroskan II plate reader at 460 nm following excitation at 355 nm. The protocol used was as for Example 2.

FIG. 9 shows that, for all three ratios of protein to chelating ISCOMATRIX, addition of E6E7hh in 4M urea resulted in an increase in the apparent size of the complex. The amount of protein added did, however, affect the final apparent diameter (as also found in Example 5). For the 1400:125 $\mu$g formulation the change was from 52 nm to 114 nm, from 52 nm to 170 nm for 1400:250 $\mu$g, and from 52 nm to 545 nm for 1400:500 $\mu$g. Following removal of the urea by dialysis, a further size increase was apparent, although this was not as large. Once formed, however, the complexes remained stable with respect to apparent size at both 4° and 31° for at least 45 days. This contrasts with the data presented in Example 8 where higher ratios of protein to chelating ISCOMATRIX were examined.

FIGS. 10a–e show the analysis of sucrose gradient fractions from all three formulations at day 0 (timed from the removal of urea by dialysis), day 6 for samples stored at both 4° and 31°, (day 28 data was essentially similar and is not shown), and day 45 for samples stored at both 4° and 31°. As with the analysis of size distribution, it is clear that the major variable affecting the composition of the particles is the ratio of protein to chelating ISCOMATRIX. This is shown in all samples examined, and therefore can be described in detail by reference to FIG. 17a (day 0 time point) only. At the lowest ratio of protein to chelating ISCOMATRIX (1400:125) a single class of complex forms, as indicated by coincidence of all four assays to give a single peak (fractions 8–11). That is, all of the E6E7hh was located in the same fractions as the ISCOMATRIX, and also was detectable in the EIA which measured E6E7hh physically associated with the particles. In contrast, however, at the highest ratio of protein to chelating ISCOMATRIX (1400:500), two classes of complex formed The first, at the same position in the gradient as the single class of complex formed at the lowest ratio, contained relatively low amounts of E6E7hh (as detected both by EIA and CPM) and also fewer particles (although this conclusion rests on the assumption that both classes of complex are detected with similar sensitivity by the DPH assay). Most of the protein was associated with the complexes which sedimented toward the bottom of the gradient (fractions 5–7). It should be noted that these gradients were not run to equilibrium, therefore the separation is based on a combination of size and density rather than density alone. Despite the fact that most of the protein appeared in the second peak (fractions 5–7), most of the ISCOMATRIX-associated protein was detected in the first peak (fractions 8–11). This is likely to be due to the design of the assay, since a positive signal requires that a HRP-labelled Mab bind to a saponin epitope on the surface of the particle. Clearly, this could be blocked in the case of a complex containing so much E6E7hh that access is sterically hindered. At the intermediate ratio of protein to chelating ISCOMATRIX, 1400:250 $\mu$g, a similar pattern is seen, although the lower peak is less well differentiated from the first peak (fractions 8–11) and is better detected by the assay for particle-associated E6E7hh, suggesting that the complexes are not as large and/or dense as those of the lower peak of the 1400:500 $\mu$g formulation. Again, this is consistent with the measured size distributions (FIG. 9).

With regard to the suitability of the formulations for vaccine usage, at each of the 3 protein to chelating ISCOMATRIX ratios, the formulations were uniform and homogenous. At the 1400:125 $\mu$g ratio the visible appearance was clear, at 1400:250 $\mu$g slightly translucent, and at 1400:500 $\mu$g cloudy. At the 1400:500 $\mu$g ratio the complexes remained as a suspension for at least a day before eventually settling to the bottom of the container. They were easily resuspended with a flick of the wrist, and once resuspended, exhibited the same settling behaviour.

EXAMPLE 12

One of the features of the ISCOM adjuvant system is its ability to deliver proteins to antigen presenting cells for processing by mechanisms which result in the generation of cytotoxic T-lymphocyte responses. This is obviously of prime importance to vaccines which depend on the induction of CTL for efficacy. The first requirement for an ISCOM-based vaccine to induce a CTL response is that it be linked (in some fashion) to the protein, so that it can play the role of a facilitating agent. A minimum requirement must be that the protein and the ISCOM enter the same antigen presenting cell. This is supported by experimental evidence from a number of systems in which ISCOMs (with incorporated antigen) have been shown to be superior to ISCOMATRIX mixed with antigen for the induction of CTL responses. One major exception is the E6E7hh protein which does in fact induce CTL when mixed with ISCOMATRIX. However, high doses of this protein are required (at least 10 $\mu$g). In addition, the fact that E6E7hh is soluble only in the presence of denaturant means that it will precipitate on injection, suggesting the possibility that the CTL responses that are induced result from trapping of ISCOMATRIX within insoluble protein aggregates. Thus, any CTL responses that are seen could represent the outcome of a non-specific and uncontrollable physical association between ISCOMATRIX and protein that occurs as soon as the denaturant diffuses following injection.

The properties of E6E7hh have meant that it has not been possible to incorporate it into ISCOMs by conventional means, therefore the availability of chelating ISCOMATRIX affords the first opportunity to test the benefits of incorporation. In practical terms, an enhanced CTL response due to chelating ISCOMATRIX over a formulation that already is at least partially capable of inducing CTL provides a rigorous and demanding test of the immunogenic advantages of chelating MATRIX. In this example, the CTL responses induced by identical doses of E6E7hh (0.75 μg, 1.5 μg, and 3 μg) formulated with either 6 μg of chelating ISCOMATRIX (batch ch10-1207, as prepared in Example 9) or mixed with 6 μg of ISCOMATRIX (batch M-1207, as prepared in Example 9) were compared. Also tested was 10 μg of E6E7hh mixed with 6 μg of ISCOMATRIX, which is a standard formulation, and was expected to result in induction of CTL. ISCOMs prepared with palmitic acid-derivatized ovalbumin were used to induce CTL specific for the target cell line used as a negative control (OVAexpressing EL4), and served as a check that these were fully susceptible to killing by CTL.

The doses were prepared by adding equal volumes of E6E7hh in 8M urea, 50mM Tris, 50 mM sodium phosphate, 150 mM NaCl pH 6.9, and either ISCOMATRIX or chelating ISCOMATRIX in 50 mM Tris, 50 mM sodium phosphate, 150 mM NaCl pH 6.9, and mixing at room temp. for 1 hr. The chelating ISCOMATRIX formulations were the dialysed overnight at 4° against 50 mM Tris, 50 mM Pi, 150 mM NaCl, 0.5% 2-phenoxyethanol, pH 6.9 in order to remove the urea, whereas the ISCOMATRIX formulations included 4M urea. For each immunization, the formulations were diluted to dose concentration with either 50 mM Tris, 50 mM sodium phosphate, 150 mM NaCl, pH 6.9, or 4M urea, 50 mM Tris, 50 mM sodium phosphate, 150 mM NaCl pH 6.9.

Groups of 5 mice were dosed subcutaneously with 0.1 ml according to the following schedule:

| Day # | Procedure |
| --- | --- |
| 0 | 1° Dose |
| 21 | 2° Dose |
| 28 | 3 mice/group tested for serological and CTL responses |
| 29 | 3° Dose |
| 36 | 2 mice/group tested for serological and CTL responses |

Figure 12:
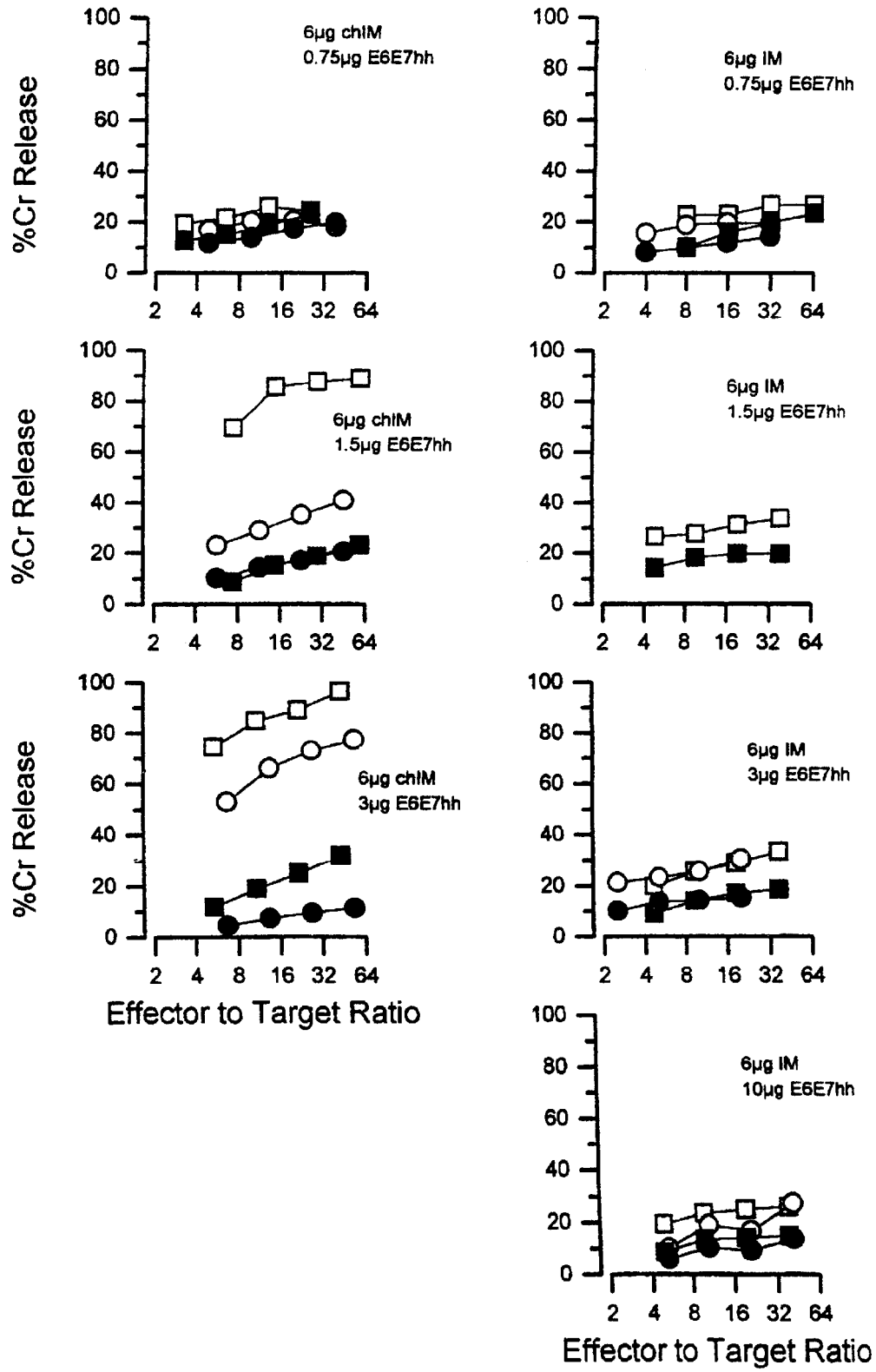
FIG. 12 shows CTL responses after three doses. Groups as for FIG. 11 but no group G.

Using the spleen cell in vitro restimulation protocol described in Example 3, individual mice were evaluated for their CTL responses to E6E7hh at the time points shown above. FIG. 11 shows that, after two immunizations, chelating ISCOMATRIX was a significantly more effective adjuvant for the generation of CTL responses to E7 than was conventional ISCOMATRIX. In fact, none of the mice immunized with ISCOMATRIX formulations generated a detectable response at these low doses of E6E7hh (0.75 μg, 1.5 μg, and 3 μg). The only response detected was with 10 μg of E6E7hh, which is in line with previous data from this system. This conclusion was similar when CTL were examined following three immunizations. FIG. 12 shows that in fact the only CTL that were detected came from mice that had been immunized with the chelating ISCOMATRIX preparations.

Figure 13:
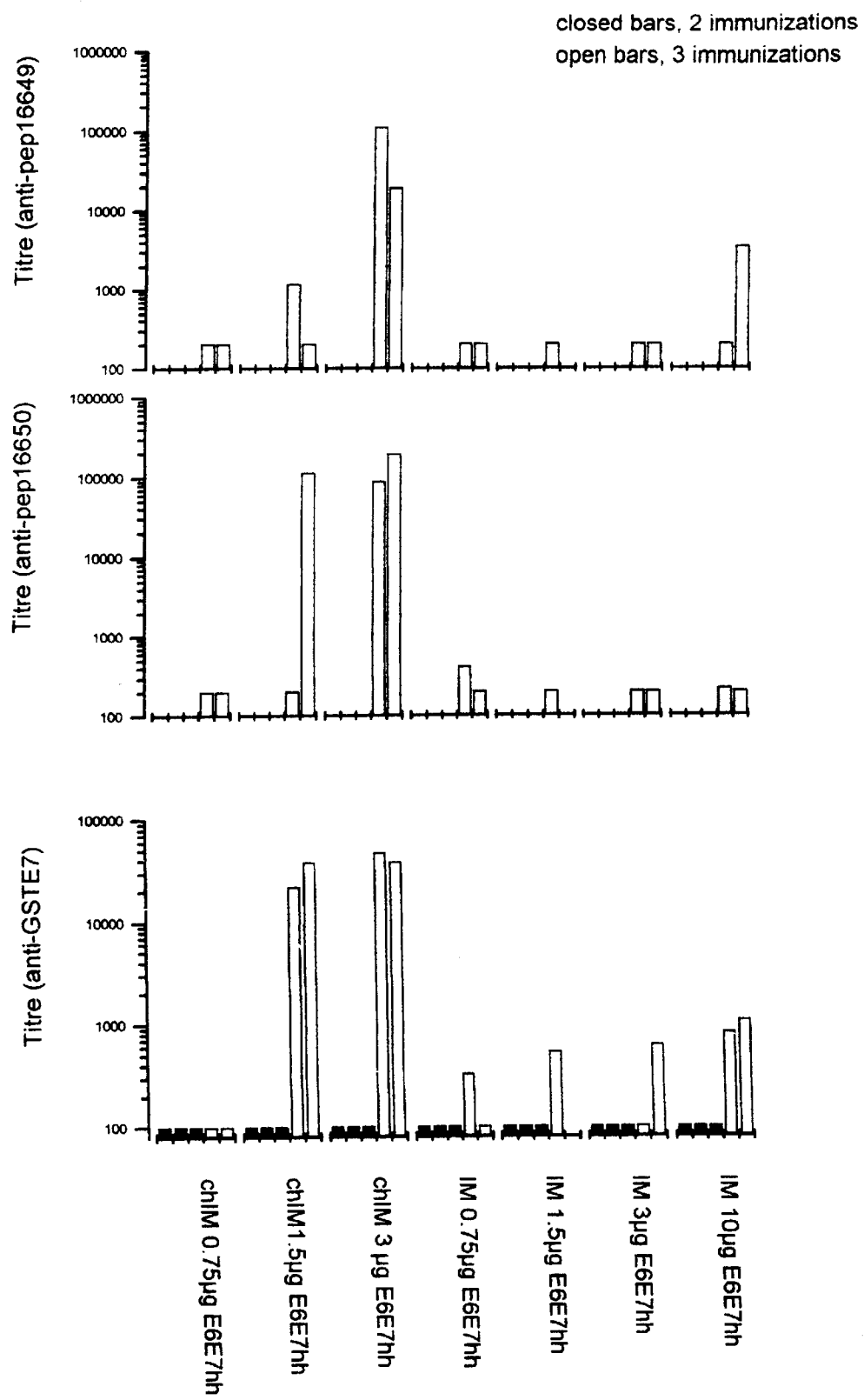
FIG. 13 shows antibody responses for ChIMX and IMX mixed with increasing amounts of E6E7hh. A: anti-peptide 16649; B: anti-peptide 16650; C: anti E7.

Antibody to E7 (assayed against GST-E7 using a solid phase EIA) was not detected in any mice until after the third immunization, however at this point the chelating ISCOMATRIX formulations were superior by a large margin (FIG. 13, bottom panel). This result was obtained in an EIA in which HPV16 GST-E7 was bound to a solid phase. Since the conventional ISCOMATRIX (but not the chelating ISCOMATRIX) formulations included urea, the possibility existed that antibodies induced by E6E7hh in urea were not adequately detected when assayed against GST-E7 protein. To formally exclude this as a possibility, sera were assayed for binding against two synthetic peptides from the HPV16 E7 sequence. In this assay, 96 well plates were coated with streptavidin, and used to bind biotinylated synthetic peptides.

After blocking with casein, sera were assayed using the same protocol used for GST-E7.

FIG. 13 (top panel) shows results with peptide "biotin-SGSG-MHGDTPTLHEYMLDQPE" (pep16649, representing residues 1–18 of the E7 sequence). FIG. 13 (centre panel) shows results with peptide "biotin-SGSG-EIDGPAGQAEPDRAHYNI" (pep16650, representing residues 37–54 of the E7 sequence). Chelating ISCOMATRIX induced high titered antibodies against both of these peptides, and again was clearly superior to conventional ISCOMATRIX.

Figure 14:
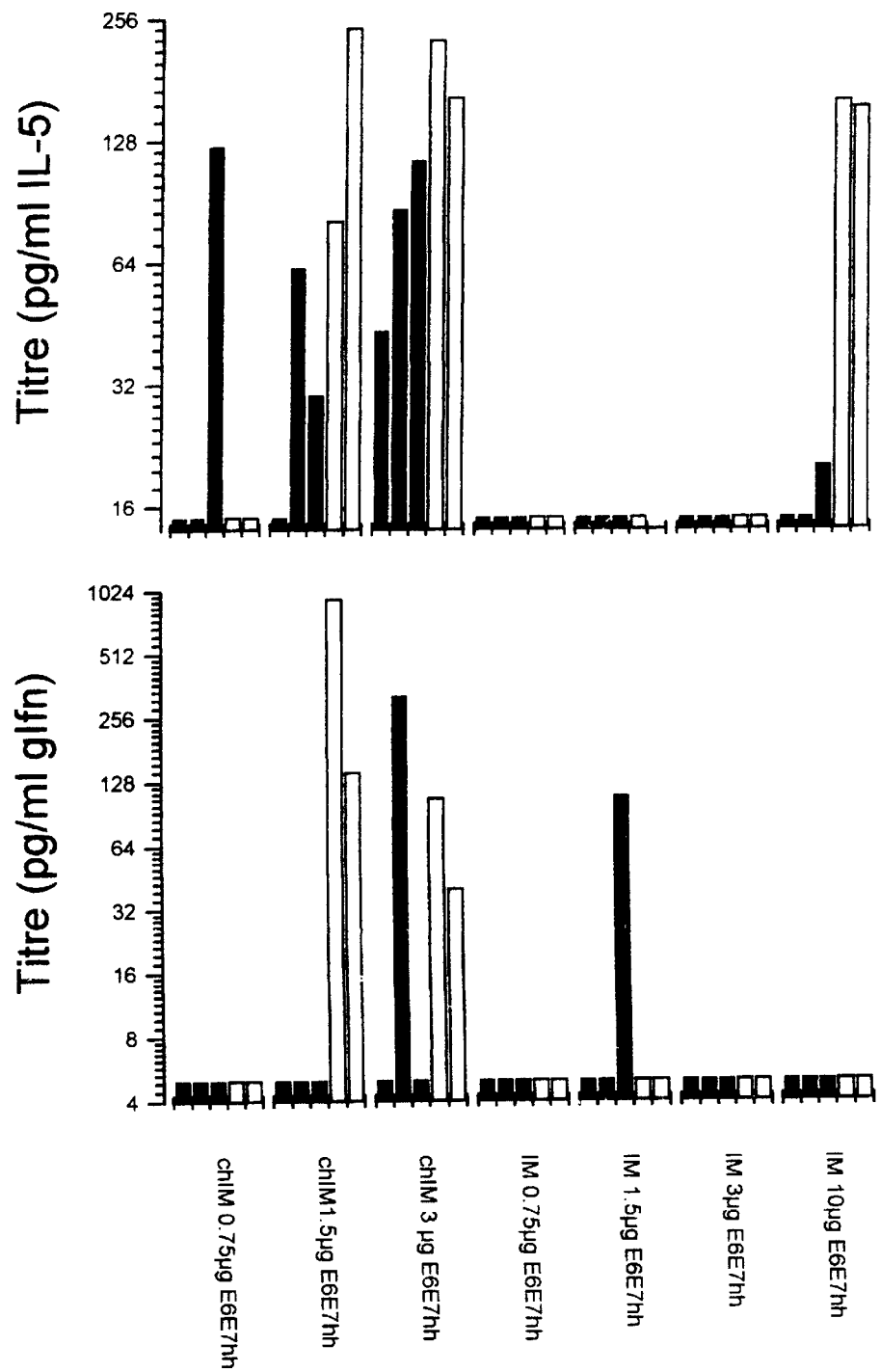
FIG. 14 Cytokine responses for the preparation used in FIG. 13. A: IL-5 response; B: γIFN response.

IL-5 and ylfn responses were examined following in vitro restimulation of spleen cells with either E6E7hh or GST-E7 following both 2 and 3 immunizations with each of the formulations (FIG. 14). Again, immunization with chelating ISCOMATRIX resulted in significantly higher responses for both IL-5 and ylfn than did immunization with conventional ISCOMATRIX.

The conclusion from this series of experiments is that chelating ISCOMATRIX is a substantially better adjuvant for both CTL and antibody responses than is conventional ISCOMATRIX. Taken together with the data presented in Examples 3 and 10 (which demonstrated that chelating ISCOMATRIX was an effective adjuvant, but did not examine the responses with low antigen concentrations and/or optimized formulations), it can be concluded that chelating ISCOMATRIX represents a significant improvement over existing technology.

EXAMPLE 13

ISCOPREP703 is a highly purified fraction derived from QuilA, which is a relatively crude extract from the bark of the Quillaia saponaria Molina tree, and is available commercially. Chelating ISCOMATRIX can also be formulated using QuilA in place of ISCOPREP703, using the methodology described in Example 9. Furthermore, chelating ISCOMATRIX made from QuiLA was fully capable of binding (His)$_6$-containing protein.

The following solutions were prepared:
1. 200 mg/ml Mega-10, 10 mg/ml cholesterol, 10 mg/ml DPPC, in 150 mM NaCl, 50 mM TRIS, 0.6 mM CuCl$_2$.2H$_2$O, pH7.2.
2. 200 mg/ml Mega-10, 10 mg/ml cholesterol, 9 mg/ml DPPC, 1.26 mg/ml DPIDA in 150 mM NaCl, 50 mM TRIS, 0.6 mM CuCl$_2$.2H$_2$O, pH7.2.
3. 50 mg/ml Quil-A saponin in 150 mM NaCl, 50 mM TRIS, pH7.2.

These solutions were combined while mixing in the following order:

Preparation 1 (ISCOMATRIX) Batch# QA00-1511

1600 μl 50 mM TRIS, 150 mM NaCl, 0.6 mM CuCl$_2$.2H$_2$O, pH7.2.

200 μl of #1

200 μl of #3

Preparation2(chelatingISCOMATRIX) Batch#QA10-1511.
1600 µl 50 mM TRIS, 150 mM NaCl, 0.6 mM CuCl$_2$.2H$_2$O, pH7.2.
200 µl of #2
200 µl of #3
The final composition of mixtures were:

|  | Preparation A (ISCOMATRIX) batch QA00-1511 | Preparation B (chelating ISCOMATRIX) batch QA10-1511 |
|---|---|---|
| ISCOPREP703 ™ | 5 mg/ml | 5 mg/ml |
| cholesterol | 1 mg/ml | 1 mg/ml |
| DPPC | 1 mg/ml | 0.9 mg/ml |
| DPIDA | not added | 0.126 mg/ml |
| CuCl$_2$.2H$_2$O | 5.4 mM | 5.4 mM |
| Mega-10 | 20 mg/ml | 20 mg/ml |

The mixtures were incubated for 90 min at room temperature, then dialysed for 16 hr against 2 liters of 50 mM TRIS, 150 mM NaCl pH 7.2 at room temperature using 12,000 molecular weight cutoff dialysis membrane, and then twice for 24 hr at 4° against 2 liters of 50 mM TRIS, 50 mM sodium phosphate, 150 mM NaCl, pH 6.9. Size distributions and copper analysis demonstrated the successful formation of chelating ISCOMATRIX:
Preparation 1 (Batch# QA00-1511).
17 µM copper
42 nm diameter
Preparation 2 (Batch# QA10-1511).
100 µM copper, representing 74% of the theoretical maximum (assuming that all DPIDA added to the formulation is incorporated into the particles, 100% of chelating sites are occupied, and the assay used measures chelated copper as efficiently as free copper).
38 nm diameter
The capacity of QuilA- chelating ICOMATRIX to bind (SEQ ID NO: 4) (His)$_6$-tagged E6E7 was then evaluated. E6E7hh at 1370 µg/ml in 10 mM TRIS, 50 mM sodium phosphate, 0.5M NaCl, 8M urea, pH 7.5 was diluted to 62.5 µg/ml with 50 mM TRIS, 50 mM sodium phosphate, 150 mM NaCl, 8M urea, pH 6.9. Two hundred µl of E6E7hh protein was then mixed with an equal volume of:
1. ISCOMATRIX (Batch#QA00-1511)
2. Chelating ISCOMATRIX (Batch #QA10-1511)
3. Chelating ISCOMATRIX (Batch #QA10-1511) in the presence of 250 mM imidazole.

The volume of the formulations was then made up to 1 ml with 50 mM TRIS, 50 mM sodium phosphate, 150 mM NaCl, 4M urea, pH 6.9 to result in a final QuilA content of approximately 500 µg/ml.

Figure 15:
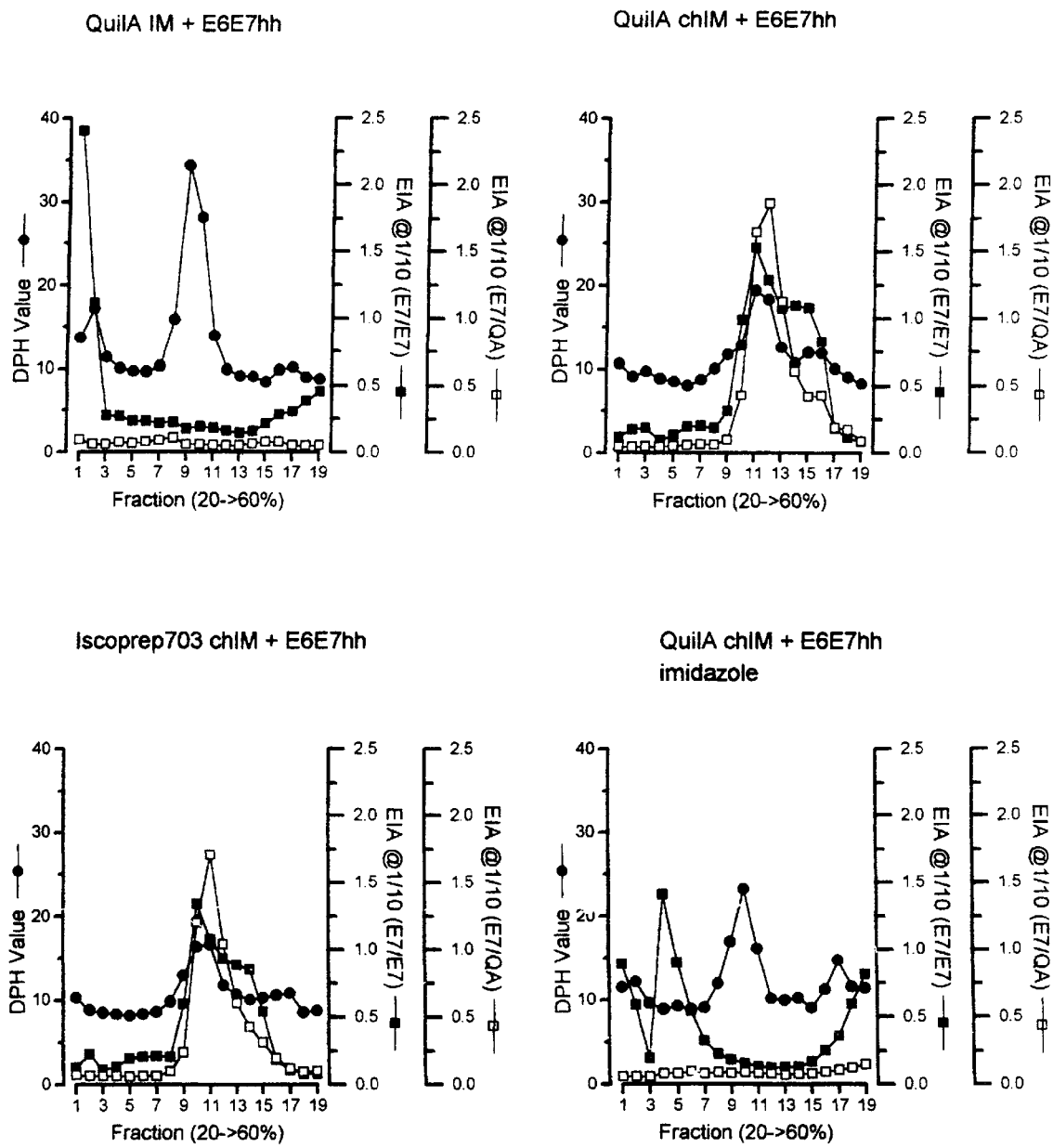
FIG. 15 shows analysis of sucrose gradient fractions of E6E7hh mixed with A: QuilA IMX; B: Quil A ChIMX; C: Iscoprep 703 ChIMX; D: Quil A ChIMX plus imidazole. ● matrix; ■ Total E6E7hh; □ E6E7hh associated with matrix.

The mixtures were incubated for 1 hour, then 0.25 ml was applied to the top of a 20–60% w/v gradient of sucrose in 50 mM TRIS, 50 mM sodium phosphate, 150 mM NaCl, pH 6.9, and centrifuged at 35,000 rpm for 15 hr in a Beckman SW40 rotor. Individual fractions were collected and assayed for ISCOMATRIX, total amount E6E7hh and ISCOMATRIX-associated E6E7hh (using the assays described in detail in previous examples). For all four preparations, there is a single well defined chISCOMATRIX or ISCOMATRIX peak centred on fractions 8–10 (FIG. 15). With the formulation of chelating ISCOMATRIX plus E6E7, there is a clear association of E6E7 with the chISCOMATRIX, as revealed by the coincidence of the total E6E7 (E7/E7 EIA) and the ISCOMATRIX-associated E6E7 (E7/QA). In contrast, the profiles of the two control formulations were markedly different. For both ISCOMATRIX plus E6E7 and chelating ISCOMATRIX plus E6E7 in the presence of imidazole, there was very little E6E7 present in the fractions containing ISCOMATRIX, and ISCOMATRIX-associated E6E7 was virtually undetected.

This analysis provides clear evidence for binding of E6E7hh to chelating ISCOMATRIX formulated with Quil-A saponin.

REFERENCES

Cox, J. C. and Coulter, A. R. (1992), "Advances in Adjuvant Technology and Application", in Animal Parasite Control Utilizing Biotechnology, Chapter 4, Ed. Yong, W. K. CRC Press.
Brenner, A. J. and Harris, E. D. (1995), *Analytical Biochemistry*, 226, 80.
Dalsgaard, K. (1974), *Arch. Gesamte Virusforsch*, 44, 243.
Dietrich, C., et al. (1995), *Proc. Natl. Acad. Sci.*, 92, 9014.
Dietrich, C., et al. (1996), *Biochemistry*, 35, 11100.
Fischer, B. E., et al. (1979), *Eur. J. Biochem.*, 94, 523.
Kensil, C. A. et al. (1988), International Patent Application No. PCT/US88/01842.
Kensil, C. A. et al. (1988), *J. Immunol.*, 146, 431.
Kersten, G. F. A. et al. (1990). "Aspects of Iscoms. Analytical, Pharmaceutical and Adjuvant Properties; Thesis, University of Utrecht.
Kubalek, E. W., et al. (1994), *J. Structural Biol.*, 113, 117.
Ng, K., et al. (1995), *Langmuir*, 11, 4048.
Pack, D. W. and Arnold, F. H. (1997), *Chemistry and Physics of Lipids*, 86, 135.
Porath, J. (1992), *Protein Expression and Purification*, 3, 263.
Scheller, K. H., et al. (1989), *Eur. J. Biochem.*, 107, 455.
Schmitt, L. et al. (1994), *J. Am. Chem. Soc.*, 116, 8485.
Shnek, D. R., et al. (1994), *Langmuir*, 10, 2382.

What is claimed is:

1. An immunostimulating complex matrix comprising a saponin preparation, a sterol and a phospholipid, said matrix further comprising a metal-chelating moiety that is (i) capable of binding a protein or polypeptide having at least one chelating amino acid sequence in the presence of metal ions and (ii) does not mask all coordination sites of said metal ions.

2. A matrix according to claim 1, wherein said metal-chelating moiety comprises:
   a. a hydrophobic sequence which anchors the molecule in the matrix;
   b. a metal-chelating headgroup; and optionally
   c. a spacer region which separates the chelating headgroup from the surface of the matrix.

3. A matrix according to claim 2, wherein said metal-chelating headgroup is a chelating iminodiacetic acid.

4. A matrix according to claim 3, wherein said metal-chelating headgroup is 1,2-distearyl-rac-glycerol-3-(8-(3,6-dioxy)octyl-1-amino-N,N-diacetic acid) ("DSIDA") or 1,2-dipalmitoyl-rac-glycerol-3-(8-(3,6-dioxy)octyl-1-amino-N,N-diacetic acid) ("DPIDA").

5. A matrix according to claim 2, wherein said metal-chelating headgroup is N-nitrilotriacetic acid.

6. A matrix according to 1, wherein the saponin preparation is QuilA.

7. A matrix according to claim 1, wherein the saponin preparation is a purified saponin preparation derived from *Quilaja saponiaria*, or a fraction or mixture thereof.

8. A matrix according to claim 1, wherein the sterol is cholesterol.

9. A matrix according to claim 1, wherein the phospholipid is dipalmitoyl phosphatidyl choline (DPPC).

10. An immunogenic immunostimulating complex which comprises a matrix according to claim 1, and an immunogenic protein or polypeptide having at least one chelating amino acid sequence, said protein or polypeptide being bound to said matrix in the presence of metal ions.

11. A complex according to claim 10, wherein said protein or polypeptide comprises a polyhistidine sequence.

12. A complex according to claim 10, wherein said protein or polypeptide is a recombinant protein or polypeptide.

13. A complex according to claim 10, wherein said protein or polypeptide is a naturally-occurring protein or polypeptide having a polyhistidine sequence chemically attached thereto.

14. A complex according to claim 10, wherein said protein or polypeptide is bound to the matrix in the presence of divalent metal ions.

15. A matrix according to claim 1, further comprising one or more adjuvants, immunosuppressive agents or other immunomodulating agents.

16. A vaccine composition for use in eliciting an immune response in humans or animals, comprising as the active component thereof an immunogenic immunostimulating complex according to claim 10, together with one or more pharmaceutically and/or veterinarily acceptable carriers and/or diluents.

17. A method of eliciting an immune response in humans or animals, which comprises the administration of an immunologically effective amount of an immunogenic immunostimulating complex according to claim 10.

18. A matrix according to claim 7, wherein said purified saponin preparation is QH703.

19. A complex according to claim 14, wherein said divalent metal ions are selected from the group consisting of $Cu^{++}$, $Ni^{++}$, $Zn^{++}$ and $Co^{++}$.

20. A matrix according to claim 1, further comprising a protein or polypeptide having at least one chelating amino acid sequence, wherein said protein or polypeptide is not covalently bound to said metal-chelating moiety.

* * * * *

SEQUENCE LISTING

<160> NUMBER OF SEQ ID NOS: 6

<210> SEQ ID NO 1
<211> LENGTH: 266
<212> TYPE: PRT
<213> ORGANISM: Human papillomavirus type 16

<400> SEQUENCE: 1

```
Met His Gln Lys Arg Thr Ala Met Phe Gln Asp Pro Gln Glu Arg Pro
 1               5                  10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
            130                 135                 140

Ser Cys Cys Arg Ser Ser Arg Thr Arg Arg Glu Thr Gln Leu Pro Gly
145                 150                 155                 160

Met His Gly Asp Thr Pro Thr Leu His Glu Tyr Met Leu Asp Leu Gln
                165                 170                 175

Pro Glu Thr Thr Asp Leu Tyr Cys Tyr Glu Gln Leu Asn Asp Ser Ser
            180                 185                 190

Glu Glu Glu Asp Glu Ile Asp Gly Pro Ala Gly Gln Ala Glu Pro Asp
            195                 200                 205

Arg Ala His Tyr Asn Ile Val Thr Phe Cys Cys Lys Cys Asp Ser Thr
            210                 215                 220

Leu Arg Leu Cys Val Gln Ser Thr His Val Asp Ile Arg Thr Leu Glu
225                 230                 235                 240

Asp Leu Leu Met Gly Thr Leu Gly Ile Val Cys Pro Ile Cys Ser Gln
                245                 250                 255

Lys Pro Arg Ser His His His His His His
            260                 265

<210> SEQ ID NO 2
<211> LENGTH: 131
<212> TYPE: PRT
<213> ORGANISM: Helicobacter pylori

<400> SEQUENCE: 2

Met Ala Ile Ser Lys Glu Glu Val Leu Glu Tyr Ile Gly Ser Leu Ser
 1               5                  10                  15

Val Leu Glu Leu Ser Glu Leu Val Lys Met Phe Glu Glu Lys Phe Gly
            20                  25                  30

Val Ser Ala Thr Pro Thr Val Val Ala Gly Ala Ala Val Ala Gly Gly
            35                  40                  45

Ala Ala Ala Glu Ser Glu Glu Lys Thr Glu Phe Asn Val Ile Leu Ala
    50                  55                  60

Asp Ser Gly Ala Glu Lys Ile Lys Val Ile Lys Val Val Arg Glu Ile
65                  70                  75                  80

Thr Gly Leu Gly Leu Lys Glu Ala Lys Asp Ala Thr Glu Lys Thr Pro
                85                  90                  95
```

His Val Leu Lys Glu Gly Val Asn Lys Glu Ala Glu Thr Ile Lys
            100                 105                 110

Lys Lys Leu Glu Glu Val Gly Ala Lys Val Glu Val Lys His His His
        115                 120                 125

His His His
    130

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (10)
<223> OTHER INFORMATION: Beta alanine

<400> SEQUENCE: 3

Ser Gly Ser Gly Lys Lys Tyr Lys Lys Ala His His His His His
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6-His tag

<400> SEQUENCE: 4

His His His His His His
1               5

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Ser Gly Met His Gly Asp Thr Pro Thr Leu His Glu Tyr Met
1               5                   10                  15

Leu Asp Gln Pro Glu
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Ser Gly Glu Ile Asp Gly Pro Ala Gly Gln Ala Glu Pro Asp
1               5                   10                  15

Arg Ala His Tyr Asn Ile
            20